United States Patent
Schlom et al.

(10) Patent No.: US 9,725,494 B2
(45) Date of Patent: Aug. 8, 2017

(54) SOLUBLE CD27 (SCD27) AND THE USE THEREOF

(71) Applicant: THE UNITED STATES OF AMERICA, as represented by the Secretary, Department of Health and Human Services, Washington, DC (US)

(72) Inventors: Jeffrey Schlom, Potomac, MD (US); Jianping Huang, Rockville, MD (US)

(73) Assignee: United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 14/276,713

(22) Filed: May 13, 2014

(65) Prior Publication Data
US 2014/0341931 A1    Nov. 20, 2014

Related U.S. Application Data

(60) Provisional application No. 61/824,898, filed on May 17, 2013.

(51) Int. Cl.
| | | |
|---|---|---|
| G01N 33/574 | (2006.01) | |
| A61K 39/39 | (2006.01) | |
| A61K 39/00 | (2006.01) | |
| C07K 14/705 | (2006.01) | |
| A61K 38/17 | (2006.01) | |

(52) U.S. Cl.
CPC .... *C07K 14/70503* (2013.01); *A61K 38/1793* (2013.01); *A61K 39/39* (2013.01); *C07K 14/70578* (2013.01); *G01N 33/57434* (2013.01); *G01N 33/57488* (2013.01); *A61K 2039/55516* (2013.01); *G01N 2333/70575* (2013.01); *G01N 2333/70578* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,698,530 A * | 12/1997 | Schlom | ............ | C07K 14/70503 424/93.2 |
| 6,258,540 B1 * | 7/2001 | Lo | ............ | C12Q 1/6879 435/440 |
| 6,355,623 B2 * | 3/2002 | Seidman | ............ | A61K 31/52 514/263.4 |
| 7,247,615 B2 * | 7/2007 | Schlom | ............ | C12N 9/6445 424/85.2 |
| 7,410,644 B2 * | 8/2008 | Schlom | ............ | C12N 15/86 424/199.1 |
| 8,481,029 B2 | 7/2013 | Glennie et al. | | |
| 8,613,933 B2 * | 12/2013 | Schlom | ............ | C07K 14/4702 424/199.1 |
| 8,933,041 B2 * | 1/2015 | Panicali | ............ | A61K 39/0011 424/199.1 |
| 9,175,057 B2 * | 11/2015 | Schlom | ............ | C07K 14/4748 |
| 9,198,941 B2 * | 12/2015 | Palena | ............ | A61K 38/17 |
| 2007/0048860 A1 * | 3/2007 | Schlom | ............ | A61K 39/0011 435/320.1 |
| 2007/0134681 A1 * | 6/2007 | Liew | ............ | C12Q 1/6886 435/6.12 |
| 2010/0173324 A1 * | 7/2010 | Mori | ............ | C07K 16/2878 435/7.1 |
| 2011/0274685 A1 | 11/2011 | Keler et al. | | |
| 2013/0156768 A1 * | 6/2013 | Jure-Kunkel | ............ | A61K 45/06 424/135.1 |

FOREIGN PATENT DOCUMENTS

| | | |
|---|---|---|
| WO | WO 2008/051424 | 5/2008 |
| WO | WO 2011/130434 | 10/2011 |
| WO | WO 2012/004367 | 1/2012 |

OTHER PUBLICATIONS

Huang et al (J. Immunology, published online May 15, 2013 190: 6250-6258).*
eBioscience (Human sCD27 Instant ELISA, Oct. 7, 2012).*
Ruf et al. (Clin. Can. Res.21(4) Feb. 15, 2015).*
Murase et al. (Cancer Lett. 1998 132: 181-186).*
Gerdes et al. (Front. Oncol. Dec. 18, 2014 doi: 10.3389/fonc.2014. 00366, pp. 1-12).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
eBioscience Acquires Bender MedSystems (http://www.ebioscience.com/about/news/ebioscience-acquires-bender-medsystems. htm, downloaded Sep. 3, 2015).*

(Continued)

Primary Examiner — Peter J Reddig
(74) Attorney, Agent, or Firm — Klarquist Sparkman, LLP

(57) ABSTRACT

Disclosed are methods of diagnosing a subject as having a solid tumor or a predisposition to developing a solid tumor. The methods include detecting or quantitating the amount of sCD27 in a serum sample obtained from a subject and comparing that amount of sCD27 with a control value indicative of the basal level of sCD27 present in the serum of a subject that does not have a solid tumor or a predisposition to developing a solid tumor, wherein a reduction of the amount of sCD27 relative to the control value indicates that the subject has the solid tumor or the predisposition to developing the solid tumor. The disclosed methods can be used to monitoring disease progression in a subject or determine a subject's suitability for immunotherapy. Also disclosed are methods of stimulating a subject's immune system by administering a therapeutically effective amount of sCD27 or a functional fragment.

18 Claims, 10 Drawing Sheets

(56) References Cited

OTHER PUBLICATIONS

Huang et al. (Blood Aug. 28, 2012 120 (15): 3030-3038).*
Gulley et al. (Cancer Immunol. Immunother. 2010 59: 663-675).*
Schenk-Braat et al. (Cancer Immunol. Immunother. 2005 54: 414-423).*
Riether et al. (Immunology Sep. 2012 137 (suppl 1): 603, Abstract P1332).*
Ciccarelli, et al., "Soluble CD27 is a faithful marker of disease burden, and is unaffected by the rituximab-induced IgM flare, as well as by plamapheresis, in patients with Waldenstrom's Marcoglulinemia," *Clinical Lymphoma* 9: 56-58 (2009).
Claus, et al., "CD27 signaling increases the frequency of regulatory T cells and promotes tumor growth," *Cancer Res.* 72: 3664-3676 (2012).
Dang, et al., "Soluble CD27 induces IgG production through activation of antigen-primed B cells," *J. Intern. Med.* 271: 283-293 (2012).
De Milito, et al., "Plasma levels of soluble CD27: a simple marker to monitor immune activation during potent antiretroviral therapy in HIV-1 infected subjects," *Clin. Exp. Immunol.* 127: 486-494 (2002).
Denoeud, et al., "Role of CD27/CD70 pathway of activation in immunity and tolerance," *J. Leukocyte Biol.* 89: 195-203 (2011).
Diegmann, et al., "Immune escape for renal carcinoma: CD79 mediates apopotosis in lymphocytes," *Neoplasia* 8: 993-998 (2006).
Font, et al., "Elevated soluble CD27 levels in serum of patients with systemic lupus erythematosus," *Clin. Immunol. Immunopathol.* 81: 239-243 (1996).
Held-Feindt, et al., "CD70/CD27 ligand, a member of the TNF family, is expressed in human brain tumors," *Int. J. Cancer* 98: 352-356 (2002).
Ho, et al., "CD27-CD70 interactions in the pathogenesis of Waldenstrom macroglobulinemia," *Blood* 112: 4683-4689 (2008).
Huang, et al., "Irradition enhances human T cell function by up-regulating CD70 expression on antigen-presenting cell in vitro," *J. Immunother.* 34: 327-335 (2011).
Huang, et al., "Soluble CD27-Pool in Humans May Contribute to T Cell Activation and Tumor Immunity." *The Journal of Immunology* 190: 6250-6258 (2013).
Kersten, et al., "Elevation of cerebrospinal fluid soluble CD27 in patients with meningeal localization of lymphoid malignancies," *Blood* 87: 1985-1989 (1996).
Murase, et al., "Increased levels of CSF soluble CD27 in patients with primary central nervous system lymphoma," *Cancer Lett.* 132: 181-186 (1998). (Abstract Only).
NIH Clinical Trial, "A Study of CDX-1127 in patients with select solid tumor types or hematological cancers," (initiated Oct. 12, 2011 and modified through May 23, 2013, 4 pages).
Riether, et al., "Modulating CD27 to treat cancer," *Oncoimmunology* 1: 9, 1604-1606 (2012).
Van Oers, et al., "Expression and release of CD27 in B cell malignancies," *Blood* 82: 3430-3436 (1993).

* cited by examiner

SEQUENCE LISTING

<160> NUMBER OF SEQ ID NOS: 2

<210> SEQ ID NO 1
<211> LENGTH: 260
<212> TYPE: PRT
<213> ORGANISM: Homo sapiens

<400> SEQUENCE: 1

Met Ala Arg Pro His Pro Trp Leu Cys Val Leu Gly Thr Leu Val
1               5                   10                  15

Gly Leu Ser Ala Thr Pro Ala Pro Lys Ser Cys Pro Glu Arg His Tyr

```
                    20                  25                  30
Trp Ala Gln Gly Lys Leu Cys Cys Gln Met Cys Glu Pro Gly Thr Phe
                35                  40                  45
Leu Val Lys Asp Cys Asp Gln His Arg Lys Ala Ala Gln Cys Asp Pro
    50                  55                  60
Cys Ile Pro Gly Val Ser Phe Ser Pro Asp His His Thr Arg Pro His
65                  70                  75                  80
Cys Glu Ser Cys Arg His Cys Asn Ser Gly Leu Leu Val Arg Asn Cys
                85                  90                  95
Thr Ile Thr Ala Asn Ala Glu Cys Ala Cys Arg Asn Gly Trp Gln Cys
                100                 105                 110
Arg Asp Lys Glu Cys Thr Glu Cys Asp Pro Leu Pro Asn Pro Ser Leu
            115                 120                 125
Thr Ala Arg Ser Ser Gln Ala Leu Ser Pro His Pro Gln Pro Thr His
        130                 135                 140
Leu Pro Tyr Val Ser Glu Met Leu Glu Ala Arg Thr Ala Gly His Met
145                 150                 155                 160
Gln Thr Leu Ala Asp Phe Arg Gln Leu Pro Ala Arg Thr Leu Ser Thr
                165                 170                 175
His Trp Pro Pro Gln Arg Ser Leu Cys Ser Ser Asp Phe Ile Arg Ile
            180                 185                 190
Leu Val Ile Phe Ser Gly Met Phe Leu Val Phe Thr Leu Ala Gly Ala
        195                 200                 205
Leu Phe Leu His Gln Arg Arg Lys Tyr Arg Ser Asn Lys Gly Glu Ser
    210                 215                 220
Pro Val Glu Pro Ala Glu Pro Cys Arg Tyr Ser Cys Pro Arg Glu Glu
225                 230                 235                 240
Glu Gly Ser Thr Ile Pro Ile Gln Glu Asp Tyr Arg Lys Pro Glu Pro
                245                 250                 255
Ala Cys Ser Pro
            260

<210> SEQ ID NO 2
<211> LENGTH: 783
<212> TYPE: DNA
<213> ORGANISM: Homo sapiens

<400> SEQUENCE: 2
atggcacggc cacatccctg gtggctgtgc gttctgggga ccctggtggg gctctcagct      60
actccagccc ccaagagctg cccagagagg cactactggg ctcagggaaa gctgtgctgc     120
cagatgtgtg agccaggaac attcctcgtg aaggactgtg accagcatag aaaggctgct     180
cagtgtgatc cttgcatacc gggggtctcc ttctctcctg accaccacac ccggccccac     240
tgtgagagct gtcggcactg taactctggt cttctcgttc gcaactgcac catcactgcc     300
aatgctgagt gtgcctgtcg caatggctgg cagtgcaggg acaaggagtg caccgagtgt     360
gatcctcttc caaacccttc gctgaccgct cggtcgtctc aggccctgag cccacaccct     420
cagcccaccc acttacccta tgtcagtgag atgctggagg ccaggacagc tgggcacatg     480
cagactctgg ctgacttcag gcagctgcct gcccggactc tctctaccca ctggccaccc     540
caaagatccc tgtgcagctc cgatttta tt cgcatccttg tgatcttctc tggaatgttc     600
```

```
cttgttttca ccctggccgg ggccctgttc ctccatcaac gaaggaaata tagatcaaac      660
aaaggagaaa gtcctgtgga gcctgcagag ccttgtcgtt acagctgccc cagggaggag      720
gagggcagca ccatccccat ccaggaggat taccgaaaac cggagcctgc ctgctccccc      780
tga                                                                   783
```

SOLUBLE CD27 (SCD27) AND THE USE THEREOF

PRIORITY CLAIM

This claims the benefit of U.S. Provisional Application No. 61/824,898, filed May 17, 2013, which is incorporated by reference herein in its entirety.

FIELD

This disclosure relates to the detection of solid cancers, the determination of a subject's responsiveness to anticancer vaccines, and to methods for stimulating the immune system of a subject.

BACKGROUND

Cancer is the second leading cause of human death next to coronary disease in the United States. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. Cancer is soon predicted to become the leading cause of death.

Cancer is an abnormal state in which uncontrolled proliferation of one or more cell populations interferes with normal biological functioning. The proliferative changes are usually accompanied by other changes in cellular properties, including reversion to a less differentiated, more developmentally primitive state. The in vitro correlate of cancer is called cellular transformation. Transformed cells generally display several or all of the following properties: spherical morphology, expression of fetal antigens, growth-factor independence, lack of contact inhibition, anchorage-independence, and growth to high density.

A soluble form of CD27 (sCD27), a 32-kD protein identical to the extracellular domain of membrane-bound CD27, can be released after lymphocyte activation by differential splicing of the receptor protein or shedding from the cell surface by proteases. The production of sCD27 upon T-cell activation has been demonstrated previously by using anti-CD3 or a combination of anti-CD3 with anti-CD2 monoclonal antibody (MAb) to stimulate human peripheral blood mononuclear cells (PBMC) in vitro. sCD27 has been detected in serum, plasma, and urine samples from healthy individuals, and increased levels have been documented in systemic lupus erythematosus, viral infections, and lymphoid malignancies. The level of sCD27 in plasma samples has been used as a marker of disease burden in subjects with Waldenstroms macroglobulinemia and to monitor immune activation during antiretroviral therapy in subjects with HIV.

SUMMARY

Methods are disclosed herein for diagnosing a subject as having a solid tumor or an identifying predisposition to developing a solid tumor. The methods include measuring the amount of soluble CD27 (sCD27) present in a serum sample obtained from a subject, for example by detecting the amount of sCD27 present in the serum sample. In some embodiments, to determine the amount of sCD27, the sample is contacted with a specific binding agent (such as an antibody, for example a monoclonal antibody or a protein, such as CD70) that specifically binds sCD27 and the amount of the specific binding agent bound to sCD27 is detected. In some embodiments, the amount of sCD27 present in the serum sample is detected by mass spectrometry. In some embodiments, the amount of sCD27 present in the serum sample is detected by measuring the activity of sCD27 in the serum sample. This amount is compared a control value indicative of the basal level of sCD27 present in the serum of a subject that does not have a solid tumor or a predisposition for developing a solid tumor. A reduction of the amount of sCD27 relative to the control value indicates that the subject has the solid tumor or the predisposition to developing the solid tumor. The methods can also include administering a therapeutic agent to the subject, such as, but not limited to, an anti-cancer vaccine.

The disclosed methods can be used to monitor disease progression in a subject undergoing treatment for a solid tumor. In specific non-limiting examples, the tumor is a prostate or colorectal tumor. In such embodiments of the disclosed methods, the amount of sCD27 is detected and/or quantitated in first serum sample obtained from a subject at a first time point. A second serum sample is obtained from the subject at a second later time point and the amount of sCD27 present in the serum sample is detected. The amount of sCD27 detected in the first serum sample is compared with the amount of sCD27 detected in the second serum sample. An increase in the amount of sCD27 in the second sample relative to the first sample indicates that the subject is benefiting from the treatment. In specific non-limiting examples, the subject is administered a recombinant poxviral vector encoding a tumor antigen and a co-stimulatory molecule, such as PROSTVAC® (rilimogene galvacirepvec/rilimogene glafolivec). In additional non-limiting examples, the subject is administered ipilimumab.

In some embodiments, methods are also disclosed for treating a subject, wherein the method includes measuring sCD27 in a biological sample from the subject. In other embodiments, the disclosed methods can also be used in determining a subject's suitability for immunotherapy. In further embodiments, the amount of sCD27 present in a serum sample is detected and can be compared with a control value indicative of the basal level of sCD27 present in the serum of a healthy subject. A reduction of the amount of sCD27 in the serum sample obtained from the subject relative to the control value indicates that the subject would benefit less from treatment, or is not benefiting from the treatment.

Also disclosed are methods of stimulating a subject's immune system, in which a subject is administered a therapeutically effective amount of sCD27 or a functional fragment thereof that is capable of stimulating the subject's immune system. In specific non-limiting examples, the subject is administered a therapeutic agent, such as, but not limited to, a recombinant poxviral vector encoding sCD27 and another immunostimulatory molecule.

The foregoing and other features and advantages of the disclosure will become more apparent from the following detailed description, which proceeds with reference to the accompanying figures.

Figure 1A:
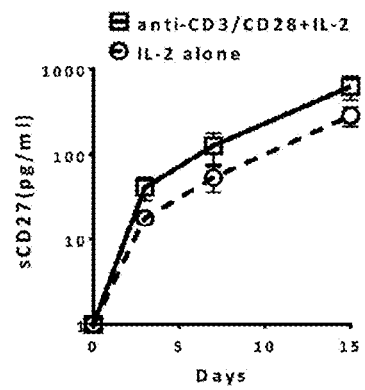
FIGS. 1A-1D. sCD27 production is associated with T-cell activation in vitro. (A) Increased sCD27 in culture supernatant from PBMCs stimulated in vitro with anti-CD3/CD28 and IL-2. Eight PBMC samples (106 cells/ml) from healthy donors were stimulated with or without anti-CD3/CD28 beads (1:1 cell-to-bead ratio) in the presence of 10 U/ml of IL-2 for 15 days. Supernatant was collected on days 3, 7, and 15. On day 7, three of the activated PBMC samples were split and fresh medium was added due to cell overgrowth, and the dilution factor was considered when calculating the values. For day 0 sCD27 values, the analysis was done using culture medium without adding serum. The level of sCD27 was tested by ELISA, and for better data presentation, the values of sCD27 are shown in log $10(y+1)$. A repeated measures ANOVA was performed on transformed data and orthogonal contrasts were used to test for linear trends on days 3-15 data only. (B) Expression of surface CD27 on T cells with or without stimulation. The cells described above were analyzed by FACS, and CD27 expression was measured by MFI of CD27 on CD3+ and propidium iodide negative (PI−) cell populations. The Y-axis is shown in log $10(y)$. A repeated measures ANOVA was performed on transformed data and pair-wise p values were adjusted using Holm's method. (C) CD70-expressing T-cell population in PBMCs with or without stimulation. FACS analysis was also done on days 0, 3, 7 and 15 for the cells described in (A) by examining the frequency of the CD3+CD70+ T-cell population in anti-CD3/CD28 and/or IL-2 stimulated PBMCs. A repeated measures ANOVA was performed on transformed data and pair-wise p-values were adjusted using Holm's method. The Y-axis is shown in log $10(y)$. (D) No significant cell death after activation with anti-CD3/CD28 beads. The experiment described in (A) was also analyzed for viability after the activation by staining the cells with PI. An example of lymphocyte (R1) and PI negative cell gates is indicated on the left and % of PI negative cell population from 10 PBMCs is shown on the right. There were no data acquired for day 15 in the IL-2 alone group in (C) and (D). Data are presented as means±SEM. MFI, mean fluorescence intensity.

FIGS. 2A-2F. Bypassing TCR engagement or CD70 blockage produced less sCD27; CD4+ T cells are the main source of sCD27 in vitro. (A) Blocking the interaction of CD27 with CD70 inhibited production of sCD27. Ten PBMC samples from healthy donors were stimulated with anti-CD3/CD28 beads and 20 μg/ml of IgG control or anti-CD70 antibody, and the supernatant was collected on day 4 post-stimulation. A two-way repeated measures ANOVA was performed on transformed data, by day. (B) PMA/ionomycin stimulation that bypasses TCR signaling produced minimal levels of sCD27 compared to anti-CD3/CD28 stimulation. Six PBMC samples (106 cells/ml) were incubated with or without PMA/ionomycin for 6 h. The supernatants were collected and analyzed by ELISA for sCD27 production, and T-cell activation was measured by intracellular production of IFN-γ in CD3+ T cells, as shown in the insert. For comparison, the same PBMCs were also stimulated with anti-CD3/CD28 and 10 U/ml of IL-2. After 3 days, the supernatants were collected and analyzed. A one-way repeated measures ANOVA was performed on transformed data. (C and D) CD4+ T cells appeared to produce a relatively greater amount of sCD27 per cell upon activation compared to CD8+ T cells. Four subsets of T cells (naïve CD4+, memory CD4+, naïve CD8+, and memory CD8+) were isolated from four PBMC samples using magnetic beads, and the subsets were stimulated with anti-CD3/CD28 in the presence of 10 U/ml of IL-2 for 7 days. The supernatants were collected on days 3 (panel C) and 7 (panel D) and evaluated for sCD27 by ELISA. Cell counts were also carried out. sCD27 production per cell was calculated (total amount of sCD27 divided by cell count). There was a highly significant difference between the CD4+ (naïve+memory) and CD8+ (naïve+memory) means on day 3 ($p<0.0001$), and a trend of a difference on day 7 ($p=0.017$). A three-factor factorial repeated measures ANOVA on the log $10(y)$ transformed data was performed for (D) and (C). Note different scale in D. (E and F) CD4+ T cells appeared to produce a relatively greater amount of sCD27 upon activation compared to CD8+ T cells. There were highly significant differences between the CD4 and CD8 means on both days ($p<0.0001$, pooled over naïve and memory cells); the difference was larger on day 7 than on day 3. Note different scale in F. The lines in the dot plots indicate the median values. *$p<0.05$ (a trend); ***$p<0.001$.

FIGS. 3A-3G. sCD27 up-regulates the expression of activation markers on T cells and promotes T cell proliferation in vitro. (A) sCD27 up-regulated surface expression of the activation marker CD25 on CD8$^+$ T cells ($p<0.0005$). Six PBMC samples were stimulated with anti-CD3/CD28 beads in the presence or absence of sCD27 (1.4 ng/ml). Three days after stimulation, FACS analysis was performed by analyzing CD25 on CD8+ T cells. A one-way repeated measures ANOVA was performed on the raw data. (B and C) sCD27 also up-regulated expression of the activation markers CD70 and 4-1BB. A two-factor factorial [sCD27 (+ or −), IL-2 (+ or −)] repeated measures ANOVA on log $10(y)$ transformed data was performed, and Holm's methods were used to adjust p-values. When the effects of sCD27 and IL-2 on CD70 and 4-1BB expression were compared, the analysis showed that sCD27 enhanced CD70 and 4-1BB expression on CD8+ T cells ($p<0.001$ and $p<0.005$, respectively), pooled over IL-2. (D) Depletion of sCD27 showed a trend of decrease in T-cell activation by measuring CD70 expression on CD8+ T cells. Four PBMC samples were stimulated with anti-CD3/CD28 beads in the presence of supernatant in which sCD27 was not depleted (sCD27 value=1.4 ng/ml, IgG$_1$) or was depleted (sCD27 value=0 pg/ml, anti-CD27) using anti-CD27 antibody. Four days later, surface expression of CD70 on CD8+ T cells was analyzed by FACS. A one-way repeated measures ANOVA was performed on transformed data, $p=0.093$. (E and F) Cells from the experiment described in (A) were also evaluated for CD40 ligand (CD40L) surface expression on CD4+ T cells by FACS analysis. sCD27 enhanced CD40L expression on CD4+ T cells measured as the percent of positive cells (panel E) or MFI (panel F). A one-way repeated measures ANOVA was performed on the raw data. (G) sCD27 promotes T-cell proliferation in vitro. Six PBMC samples from healthy donors (106 cells/ml) were labeled with CFSE and then stimulated with anti-CD3/CD28 beads at a low (1:5) bead to cell ratio in the presence of different concentrations of purified recombinant sCD27 and IL-2 (10 U/ml). The CFSE dilution was analyzed by FACS on day 5 after stimulation, and CD3+CFSE− cells were gated. Results from three of six PMBC samples are shown. Lines in the dot plot graphs indicate the median values. *$p<0.05$ (a trend); ***$p<0.001$. MFI, mean fluorescence intensity.

FIGS. 4A-4D. Serum sCD27-pools were larger in healthy donors than in cancer patients, and PROSTVAC® plus ipilimumab significantly elevated the pool in these patients. (A) sCD27 levels (analyzed by ELISA) in sera from healthy donors (n=54) were compared with pre-treatment sera from prostate cancer patients (n=50) with rising PSA but no radiographic evidence of metastases (NCT00514072 and NCT00020254), and from patients with metastatic prostate cancer (n=120) (NCT00060528 and NCT00113984). Healthy donors were age and gender matched with prostate cancer patients. Box-and-whisker plots are shown. The Y-axis is shown log $10(y+1)$ and median values are indicated. Comparison was performed using one-way repeated measures ANOVA on transformed data and Holm's method was used to adjust p-values. (B) There was a significant elevation of serum sCD27-pool after administration of PROSTVAC® plus ipilimumab. Pre- and post-treatment serum samples from 29 out of 30 patients enrolled in the trial were available for evaluation. sCD27 serum values were analyzed by ELISA, and comparisons were performed between mean values of each post-treatment blood draw: days 15 (n=29), 45 (n=29), 70 (n=24), and 100-120 (n=26) and the mean baseline (day 0) values for all patients. The data were calculated using the mean of four blinded tests and the Y-axis is shown in log 2(y). (C) An increase in peripheral blood absolute lymphocyte count (ALC) after the treatment. Analysis similar to that described in (B) was also done for ALC. (D) Values of sCD27 in serum per lymphocyte of the patients. A calculation of sCD27 per cell at each time point of blood draw was carried out by using the total amount of sCD27 in serum of each patient divided by their ALC value on the same date. The Y-axis is shown in log 2(y). For the statistical analysis, a one-way repeated measures ANOVA was performed on the transformed data. The mean of the day 0 data vs. the means of the other 4 days was compared and the p-values adjusted using Dunnett's method. $p<0.01$; *$p<0.001$. Figures show means±SEM.

FIGS. 5A-5E. Association between elevation of sCD27-pool and clinical outcome after treatment with PROSTVAC® plus ipilimumab. (A) Association between baseline CD27-pool in serum and overall survival. Separating patients into two groups, sCD27 high and sCD27 low using median values of sCD27 for day 0, Kaplan-Meier survival curves are shown for the association between sCD27 at baseline for these two groups and overall survival. (B, C and D) Association between CD27-pool enlargement in patients and overall survival after the therapy. Patients were separated into two groups: sCD27 high and sCD27 low using median increased sCD27 values (differences from day 0 baseline) for 45, 70 or 100-120 days post-treatments. The association between sCD27-pool and overall survival is shown using Kaplan-Meier survival curves, which were plotted for patients from the date of the first administration of PROSTVAC® plus ipilimumab to the date of death, or the date of the last follow-up for patients who were still alive. The graphs of days 45, 70 and 100-120 after the treatment are shown. Strata were compared using the log-rank test. The values of sCD27 used for this evaluation were from an average of four blinded ELISA assays. (E) A schematic depiction of the sCD27-pool in healthy donors and cancer patients, and its elevation after immunotherapy. The level of the sCD27-pool is >3 fold higher in healthy individuals than in cancer patients before immunotherapy. After the therapy, the pool was cumulatively refilled as more treatment cycles were given, and some patients reached above a putative threshold (a red dashed line), which is the level required for proper immune function. *$p=0.022$ (a trend).

Figure 6:
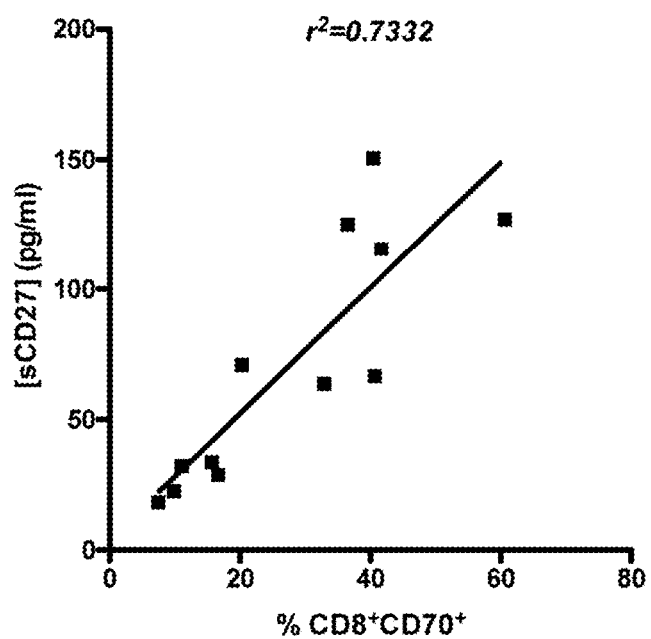

FIG. 6. sCD27 production is linearly correlated with CD70 expression on T cells. Four PBMC samples (10⁶/ml) from healthy donors were stimulated with anti-CD3/CD28 beads (1:1 bead-to-cell ratio) in the presence of IL-2 (10 U/ml) for 15 days. Supernatants and cells were collected on days 3, 6 and 15, and analyzed for the levels of sCD27 by ELISA, and for CD70 expression on CD8+ T cells by FACS analysis. Linear regression between sCD27 in the supernatant and the frequency of CD8+CD70+ cells was analyzed using data from all three time points. There was a significant correlation between CD70 expression and sCD27 in the supernatant ($p=0.0004$, $r2=0.7332$).

Figure 7A:
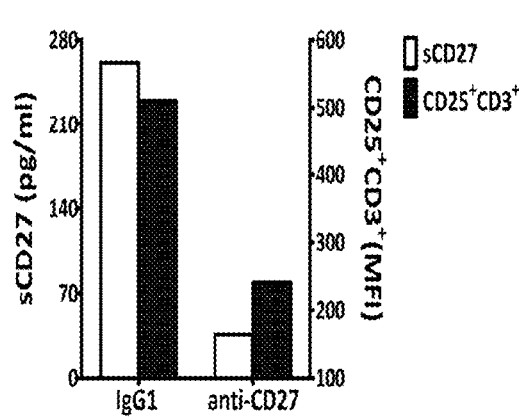
Figure 7B:
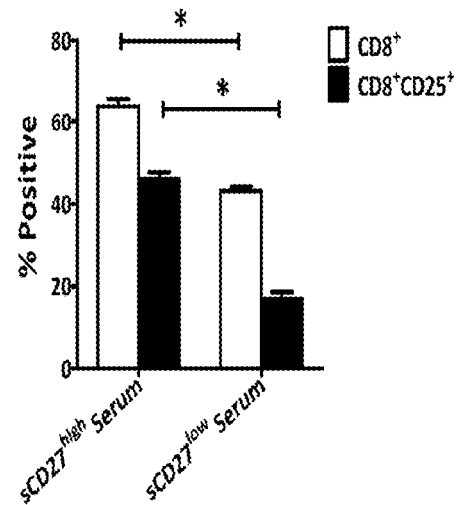

FIGS. 7A-7B. Serum containing high levels of sCD27 appears to enhance CD8+ T-cell activation in vitro. (A) CD25 expression on CD8+ T cells decreased after culturing in medium containing sCD27-depleted serum. Two wells of a 48-well plate were coated with either anti-CD27 or control IgG and left overnight at 4° C., after which the plate was washed three times with PBS. Equal amounts of sCD27 high serum were added to the two wells and left for 3 h at room temperature. PBMCs were stimulated with anti-CD3/CD28 beads (1:5 bead-to-cell ratio) and IL-2 (10 IU/ml), in medium containing serum in which sCD27 was depleted (anti-CD27) or not depleted ($IgG_1$). On day 6, surface expression of CD25 on CD8+ T cells was analyzed. The left Y axis shows the depletion efficiency for sCD27 by ELISA; the right Y axis shows CD25 surface expression on CD3+ cells, with or without sCD27 depletion. The result is representative of three separate experiments. (B) Serum from healthy donors containing high levels of sCD27 may have a greater ability to stimulate CD8+ T cells in vitro compared to serum from cancer patients, which contains low levels of sCD27. PBMCs from healthy donors were divided into two wells. sCD27 high (>1000 pg/ml) serum was added to one well and sCD27 low (<10 pg/ml) serum was added to the other well as a serum supplement (20%) for the cell cultures, in the presence of anti-CD3/CD28 beads (1:5 bead-to-cell ratio) and IL-2 (10 IU/ml). On day 16, CD8+ T cells were analyzed by FACS for CD25 surface expression, comparing the difference between cells cultured in sCD27high serum and sCD27low serum. *$p<0.05$.

Figure 8:
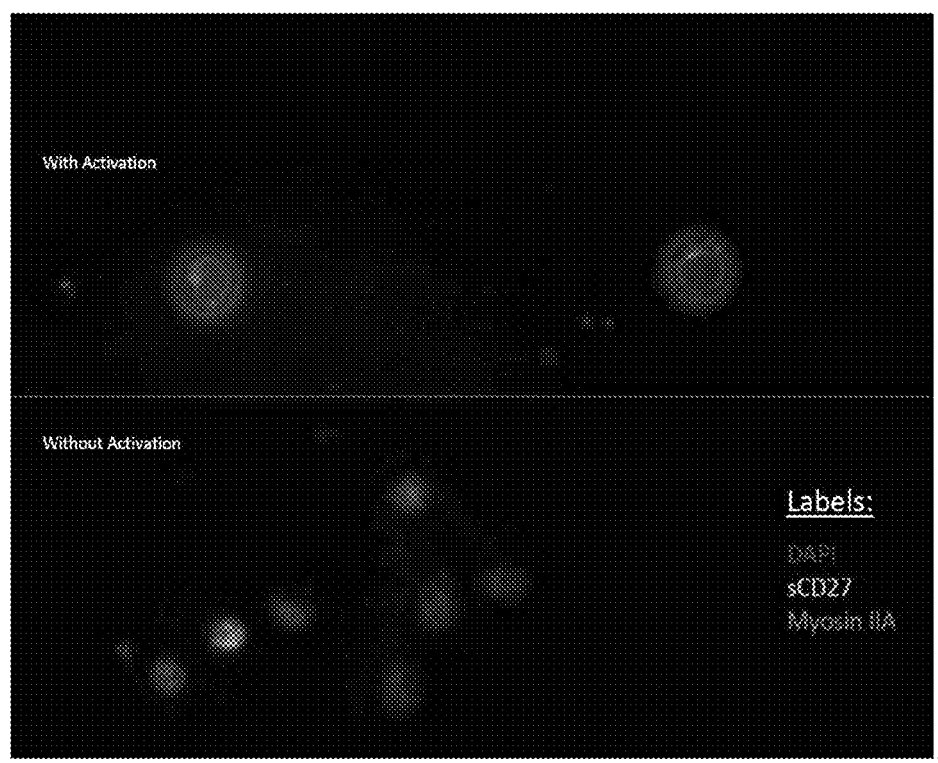

FIG. 8. The association between sCD27 and Myosin IIA in activated T cells. PBMCs from a healthy donor were stimulated with anti-CD3/CD28 beads in the presence of recombinant sCD27 containing 6× his-Tag at the carboxyl terminus of the protein, and unstimulated T cells were used as a control. After overnight stimulation, T cells were separated using a Pan T cell isolation kit. Purified T cells were stained with monoclonal mouse anti-human antibody against Myosin IIA and anti-6×-His-Biotin, followed by anti-mouse Rhodamine conjugate and Biotin-FITC staining. The nuclei of the T cells were stained with DAPI. Confocal microscopy shows co-localization of sCD27 and Myosin IIA in activated cells (top panel).

Figure 9A:
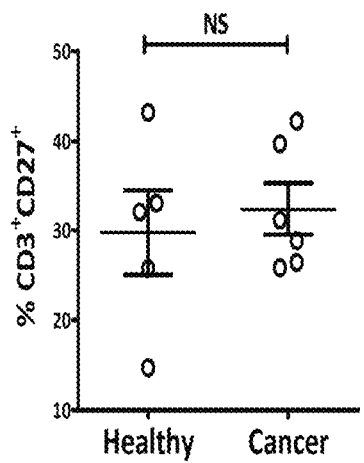
Figure 9B:
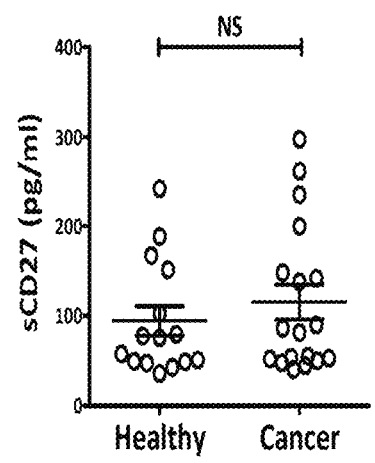

FIGS. 9A-9B. No difference in sCD27 production between healthy donors and cancer patients after in vitro stimulation of PBMCs. PBMC samples from five healthy donors and six cancer patients were stimulated with anti-CD3/CD28 beads (1:5 bead-to-cell ratio) and IL-2 (10 IU/ml). The surface expression of CD27 on CD3+ cells was evaluated by flow cytometry on day 0 (A). Culture supernatants were collected on days 3, 7 and 15, and the amount of sCD27 was evaluated by ELISA (B). There were no statistical differences between healthy donors and cancer patients, as determined by two-tailed Wilcoxon signed rank test.

Figure 10:
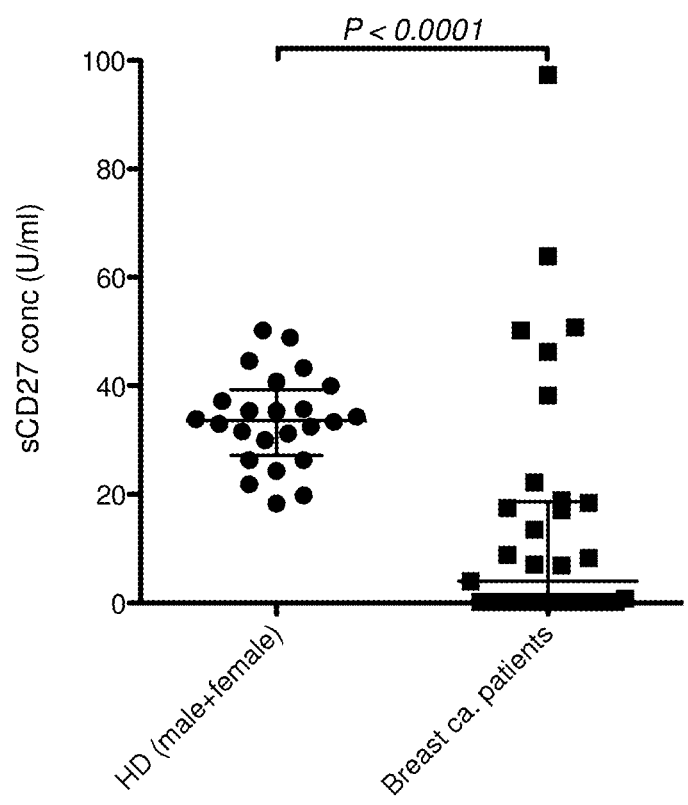

FIG. 10. Comparison of serum levels of sCD27 in healthy donors (male and female, n=24) vs. pre samples from patients with breast cancer in the PANVAC-Docetaxel trial (n=33). Dot plots show medians and interquartile range. sCD27 is increased in the subjects with breast cancer.

SEQUENCE LISTING

The nucleic acid and amino acid sequences listed herein are shown using standard letter abbreviations for nucleotide bases, and three letter code for amino acids, as defined in 37 C.F.R. §1.822. Only one strand of the nucleic acid sequence is shown, but the complementary strand is understood as included by any reference to the displayed strand.

SEQ ID NO: 1 is an exemplary amino acid sequence of human CD27.

SEQ ID NO: 2 is an exemplary nucleic acid sequence of human sCD27.

The Sequence Listing is submitted as an ASCII text file [4239-86229-02₁₃ Listing.txt, Jul. 8, 2014, 3.77 KB], which is incorporated by reference herein.

DETAILED DESCRIPTION

I. Summary of Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting To facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject. In some examples a chemotherapeutic is administered to a subject, for example a subject with a reduced immune system and/or cancer, such as a solid tumor, for example colorectal cancer or prostate cancer. In some examples, sCD27 is administered to a subject, for example a subject with cancer, such as a solid tumor, for example colorectal cancer or prostate cancer.

Animal: Living multi-cellular vertebrate organisms, a category that includes, for example, mammals and birds. The term mammal includes both human and non-human mammals. Similarly, the term "subject" includes both human and veterinary subjects. In some examples, a subject is a subject suffering from cancer, such as a solid tumor, for example or colorectal cancer prostate cancer, and/or being evaluated for cancer.

Antibody: A polypeptide ligand comprising at least a light chain or heavy chain immunoglobulin variable region which specifically recognizes and binds an epitope of an antigen or a fragment thereof, for example an epitope on sCD27. Antibodies can be composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

The term antibody includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds an antigen of interest has a specific $V_H$ region and the $V_L$ region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or a progeny thereof. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

In some examples, an antibody that specifically binds AMACR is P504S. In some examples, an antibody that specifically binds high molecular weight cytokeratin is 34βE12. In some examples, an antibody that specifically binds Sox2 is SP76.

Antibody binding affinity: Affinity of an antibody for an antigen, such as sCD27. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$ M, at least about $2.0 \times 10^{-8}$ M, at least about $2.5 \times 10^{-8}$ M, at least about $3.0 \times 10^{-8}$ M, at least about $3.5 \times 10^{-8}$ M, at least about $4.0 \times 10^{-8}$ M, at least about $4.5 \times 10^{-8}$ M, or at least about $5.0 \times 10^{-8}$ M.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T-cells respond. In one embodiment, T-cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen and/or a breast specific antigen. A tissue specific antigen may be expressed by more than one tissue, such as, but not limited to, an antigen that is expressed in both prostate and breast tissue. A disease-specific antigen is expressed coincidentally with a disease process. Specific non-limiting examples of a disease-specific antigen are an antigen whose expression correlates with, or is predictive of, tumor formation, such as prostate cancer and/or breast cancer. A disease-specific antigen can be an antigen recognized by T-cells or B-cells.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV). Tumor size staging and node involvement staging can be combined into a single clinical staging number, as exemplified below.

| Tumor size staging | Node involvement staging | Clinical stage |
| --- | --- | --- |
| T1 | N0 | I |
| T1 | N1 | IIA |
| T2 | N0 | IIA |
| T2 | N1 | IIB |
| T3 | N0 | IIB |
| T1-T2 | N2 | IIIA |
| T3 | N1 | IIIA |
| T3 | N2 | IIIA |
| T4 | N0-N2 | IIIB |

Breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, but as it progresses to "invasive," the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen, L., Petersen, O. W. & Bissell, M. J. Cellular changes involved in conversion of normal to malignant breast: importance of the stromal reaction. Physiol Rev 76, 69-125 (1996).

Breast cancers can be divided into groups based on their expression profiles. Basal-type carcinomas usually are negative for expression of estrogen receptor (ER) and negative for expression of HER2 (erbB2) and progesterone receptor (PR), and thus are referred to as "triple-negative breast cancers" or "TNBC." This type of breast cancer is also denoted $ER^-/HER2^-/PR^-$ and represents about 15-20% of all breast cancer, and generally cannot be treated using Her2 targeted or estrogen targeted therapies. It is believed that the aggressive nature of this cancer is correlated with an enrichment for cancer stem cells (CSC) with a $CD44^+CD24^{-/lo}$ phenotype. In some embodiments, basal carcinomas are negative for expression of progesterone receptor (PR), positive for expression of epidermal growth factor receptor (EGFR), and positive for expression of cytokeratin 5 (CK5). This phenotype is denoted as follows: $ER^-/PR^-/HER2^-/CK5^+/EGER^+$.

CD4: Cluster of differentiation factor 4, a T-cell surface protein that mediates interaction with the MHC Class II molecule. CD4 also serves as the primary receptor site for HIV on T-cells during HIV infection. Cells that express CD4 are often helper T-cells.

CD8: Cluster of differentiation factor 8, a T-cell surface protein that mediates interaction with the MHC Class I molecule. Cells that express CD8 are often cytotoxic T-cells.

CD27: A member of the TNF-receptor superfamily. This receptor is involved in the generation and long-term maintenance of T cell immunity. CD27 is expressed primarily on T cells, as well as on subsets of B cells and NK cells. CD70, which is expressed on activated B and T cells, but not on resting lymphocytes, is a ligand for CD27. CD27 transduces signals that lead to the activation of NF-κB and MAPK8/JNK. Adaptor proteins TRAF2 and TRAF5 have been shown to mediate the signaling process of this receptor. Cell surface CD27 can be proteolytically cleaved to produce a 32-kDa soluble CD27 (sCD27) molecule. An exemplary amino acid sequence of CD27 can be found on GEN-BANK® at Accession No. NP_001233, which is specifically incorporated by reference herein in its entirety as available Dec. 3, 2010. In one example, human CD27 has the amino acid sequence set forth below as SEQ ID NO: 1:

```
                                              (SEQ ID NO: 1)
marphpwwlc vlgtlvglsa tpapkscper hywaqgklcc qmcepgtflv kdcdqhrkaa qcdpcipgvs fspdhhtrph cescrhcnsg llvrnctita naecacrngw qcrdkectec dplpnpslta rssqalsphp qpthlpyvse mleartaghm qtladfrqlp artlsthwpp qrslcssdfi rilvifsgmf lvftlagalf lhqrrkyrsn kgespvepae peryscpree egstipiqed yrkpepacsp.
```

An exemplary nucleic acid sequence encoding CD27 can be found on GENBANK® at Accession No. NM_001242.4, which is specifically incorporated by reference herein in its entirety as available Dec. 3, 2010. In one example, a nucleic acid sequence encoding human CD27 has the nucleic acid sequence set forth below as SEQ ID NO: 2:

```
                                              (SEQ ID NO: 2)
atggcacggc cacatccctg gtggctgtgc gttctgggga ccctggtggg gctctcagct actccagccc ccaagagctg cccagagagg cactactggg ctcagggaaa gctgtgctgc cagatgtgtg agccaggaac attcctcgtg aaggactgtg accagcatag aaaggctgct cagtgtgatc cttgcatacc gggggtctcc ttctctcctg accaccacac ccggccccac tgtgagagct gtcggcactg taactctggt cttctcgttc gcaactgcac catcactgcc aatgctgagt gtgcctgtcg caatgctgg cagtgcaggg acaaggagtg caccgagtgt gatcctcttc caaaccttc gctgaccgct cggtcgtctc aggccctgag cccacaccct cagcccaccc acttacctta tgtcagtgag atgctggagg ccaggacagc tgggcacatg cagactctgg ctgacttcag gcagctgcct gcccggactc tctctaccca ctggccaccc caaagatccc tgtgcagctc cgattttatt cgcatccttg tgatcttctc tggaatgttc cttgttttca ccctggccgg ggccctgttc ctccatcaac gaaggaaata tagatcaaac aaaggagaaa gtcctgtgga gcctgcagag ccttgtcgtt acagctgccc cagggaggag gagggcagca ccatccccat ccaggaggat taccgaaaac cggagcctgc ctgctccccc tga.
```

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating prostate cancer and/or colorectal cancer. In another embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., Chemotherapy, Ch. 17 in Abeloff, *Clinical Oncology 2nd ed.*, 2000 Churchill Livingstone, Inc; Baltzer and Berkery. (eds): *Oncology Pocket Guide to Chemotherapy*, 2nd ed. St. Louis, Mosby-Year Book, 1995; Fischer Knobf, and Durivage (eds): *The Cancer Chemotherapy Handbook*, 4th ed. St. Louis, Mosby-Year Book, 1993). Combination chemotherapy is the administration of more than one agent to treat cancer, for example to treat prostate cancer and/or colorectal cancer.

Contacting: "Contacting" includes in solution and solid phase, for example contacting a sample with a specific binding agent, such as an antibody that specifically binds sCD27.

Conditions sufficient to detect: Any environment that permits the desired activity, for example, that permits an antibody to bind an antigen, such as sCD27, and the interaction to be detected. For example, such conditions include appropriate temperatures, buffer solutions, and detection means such as and digital imaging equipment.

Control: A reference standard. A control can be a known value indicative of basal levels or amounts of sCD27 present in serum, such as serum obtained from a healthy subject. A control can also be a serum control, for example serum obtained from the subject from an earlier time point. A difference between a test sample and a control can be an increase or conversely a decrease, for example a decrease or increase in the amount of sCD27. The difference can be a qualitative difference or a quantitative difference, for example a statistically significant difference. In some examples, a difference is an increase or decrease in amount, relative to a control, of at least about 1%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Costimulatory molecule: T-cell activation typically requires binding of the T-cell receptor ("TCR") with a peptide-MHC complex as well as a second signal delivered via the interaction of a costimulatory molecule with its ligand. Costimulatory molecules are molecules that, when bound to their ligand, deliver the second signal required for T-cell activation. The most well-known costimulatory molecule on the T-cell is CD28, which binds to either B7-1 or B7-2. Other costimulatory molecules that can also provide the second signal necessary for activation of T-cells include intracellular adhesion molecule-1 ("ICAM-1"), intracellular adhesion molecule-2 ("ICAM-2"), leukocyte function associated antigen-1 ("LFA-1"), leukocyte function associated antigen-2 ("LFA-2"), and leukocyte function associated antigen-3 ("LFA-3").

Cytotoxic T-Lymphocyte Antigen 4 (CTLA4): A protein receptor also known as CD152. CTLA4 is a member of the immunoglobulin superfamily, which is expressed on the surface of helper T cells and transmits an inhibitory signal to T cells. CTLA4 binds to CD80 and CD86, also called B7-1 and B7-2 respectively, on antigen-presenting cells. CTLA4 transmits an inhibitory signal to T cells. An exemplary nucleic acid sequence encoding human CTLA4, and the amino acid sequence encoded by this nucleic acid sequence, are provided in GENBANK® Accession No. NM_001037631, Apr. 29, 2013, which is incorporated herein by reference.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T-cells. Immature dendritic cells originate in the bone marrow and reside in the periphery as immature cells.

Detect: To determine if an agent (such as a signal or protein, for example sCD27) is present or absent. In some examples, this can further include quantification, for example the quantification of the amount of sCD27 in a sample, such as a serum sample, or a fraction of a sample.

Diagnostic: Identifying the presence or nature of a pathologic condition, such as, but not limited to cancer, such as a solid tumor, for example colorectal cancer and/or prostate cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (for example severity) of a pathologic condition, such as cancer (for example colorectal and/or prostate cancer), or metastasis. In some examples prognostic is the probability that a subject will respond favorably to a vaccination, such as a vaccination for cancer, such as solid tumor, for example colorectal and/or prostate cancer.

Effective amount or Therapeutically effective amount: The amount of agent, such as a chemotherapeutic agent, that is sufficient to prevent, treat (including prophylaxis), reduce and/or ameliorate the symptoms and/or underlying causes of any of a disorder or disease, for example to prevent, inhibit, and/or treat cancer, such as solid tumor, for example colorectal and/or prostate cancer. In some embodiments, an "effective amount" is sufficient to reduce or eliminate a symptom of a disease, such as prostate cancer, or an amount sufficient to achieve a desired biological effect, for example an amount that is effective to decrease the size (e.g., volume), side effects and/or metastasis of prostate cancer. In one example, it is an amount sufficient to decrease the symptoms or effects of a prostate carcinoma, such as the size of the tumor. In particular examples, it is an amount effective to decrease the size of a solid tumor, for example colorectal and/or prostate cancer and/or metastasis by at least 30%, 40%, 50%, 70%, 80%, 90%, 95%, 99% or even 100% (complete elimination of the tumor). In some examples, an effective amount of an agent is the amount of sCD27 needed to enhance a subject's immune system and/or prevent, inhibit, and/or treat cancer, such as solid tumor, for example colorectal and/or prostate cancer.

Epitope: An antigenic determinant. These are particular chemical groups or peptide sequences on a molecule that are antigenic, i.e. that elicit a specific immune response. An antibody specifically binds a particular antigenic epitope on a polypeptide, for example an epitope on the surface of sCD27. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser.

Examples of particular fluorophores that can be used in the methods and for attachment to antibodies that specifically binds sCD27 are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxy-fluorescein (5-FAM); boron dipyrromethene difluoride (BO-DIPY); N,N,N',N'-tetramethyl-6-carboxyrhodamine (TAMRA); acridine, stilbene,-6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore.

In some examples, a fluorophore is detectable label, such as a detectable label attached to an antibody.

Immunoassay: A biochemical test that measures the presence or concentration of a substance in a sample, such as a biological sample, for example a serum sample obtained from a subject, using the reaction of an antibody to its cognate antigen, for example the specific binding of an antibody to a protein, such sCD27. Both the presence of antigen or the amount of antigen present can be measured. In some examples, the amount of sCD27 is measured.

Measuring the quantity of antigen (such as sCD27) can be achieved by a variety of methods. One of the most common is to label either the antigen or antibody with a detectable label. Specific, non-limiting examples of labels include fluorescent tags, enzymatic linkages, and radioactive isotopes (for example $^{14}C$, $^{32}P$, $^{125}I$, and $^{3}H$ isotopes and the like). In some examples an antibody that specifically binds sCD27 is labeled. Methods for labeling and guidance in the choice of labels appropriate for various purposes are discussed for example in Sambrook et al. (Molecular Cloning: A Laboratory Manual, Cold Spring Harbor, N.Y., 1989) Ausubel et al. (In Current Protocols in Molecular Biology, John Wiley & Sons, New York, 1998), and Harlow & Lane, (Antibodies, A Laboratory Manual, Cold Spring Harbor Publications, New York, 1988).

Immune response: A response of a cell of the immune system, such as a B-cell, T-cell, or monocyte, to a stimulus. In one embodiment, the response is specific for a particular antigen (an "antigen-specific response"). In one embodiment, an immune response is a T-cell response, such as a CD4+ response or a CD8+ response. In another embodiment, the response is a B-cell response, and results in the production of specific antibodies.

Immunogenic peptide: A peptide which comprises an allele-specific motif or other sequence such that the peptide will bind an MHC molecule and induce a cytotoxic T lymphocyte ("CTL") response, or a B-cell response (e.g., antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein.

Inhibiting or treating a disease: Inhibiting the full development of a disease or condition, for example, cancer, such as solid tumor, for example colorectal and/or prostate cancer. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, such a metastasis, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology, for example metastatic prostate cancer, for example using a vaccine for the cancer.

Isolated: An "isolated" biological component, such as a peptide (for example sCD27), cell, nucleic acid, or serum samples has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a cell as well as chemically synthesized peptide and nucleic acids. The term "isolated" or "purified" does not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation, such as at least 50%, at least 60%, at least 70%, at least 80%, at least 90%, at least 95%, or even at least 99% of the peptide or protein concentration.

Label or Detectable label: A detectable compound or composition, which can be conjugated directly or indirectly to another molecule, such as an antibody (for example an antibody that specifically binds sCD27) or a protein, to facilitate detection of that molecule. Specific, non-limiting examples of labels include fluorescent tags, enzymes, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluoroscein istothiocyanate (FITC), rhodamine, lanthanide phosphors, cyanine dyes, fluorescent proteins, such as GFP), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition (1995), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced. In some examples, a protein is sCD27.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. In some examples, a polypeptide is sCD27.

Poxvirus: Four genera of poxviruses infect humans: *orthopox, parapox, yatapox, molluscipox*. Orthopox includes smallpox virus (variola), vaccinia virus, cowpox virus, and monkeypox virus. *Parapox* includes the orf virus, pseudocowpox, and bovine papular stomatitis virus. *Yatapox* includes tanapox virus, and yaba monkey tumor virus. *Molluscipox* includes *molluscum contagiosum* virus (MCV). Poxyiridae viral particles (virions) are generally enveloped (external enveloped virion-EEV), though the intracellular mature virion (IMV) form of the virus, which contains different envelope, is also infectious.

Vaccinia virus is used as an effective tool for heterologous protein expression. Vaccinia virus enters cells mainly by cell fusion. This virus contains three classes of genes, early, intermediate and late, that are transcribed by viral RNA polymerase and associated transcription factors. Vaccinia virus replicates its genome in cytoplasm of the infected cells and after late gene expression virion morphogenesis produces intracellular mature virion (IMV) that contains envelope, although the origin of the envelope membrane is still unknown. IMV is transported to Golgi, wherein the intracellular enveloped virus (IEV) is formed. IEV transports along microtubules to reach cell periphery and fuse with plasma membrane to become cell-associated enveloped virus (CEV) that triggers actin tails on cell surfaces or forms the extracellular enveloped virion (EEV), which is believed to be important for long range dissemination within the host organism.

Prime-boost vaccination: The term "prime-boost vaccination" refers to a vaccination strategy using a first, priming injection of a vaccine targeting a specific antigen followed at intervals by one or more boosting injections of the same vaccine. Prime-boost vaccination may be homologous or heterologous. A homologous prime-boost vaccination uses a vaccine comprising the same immunogen and vector for both the priming injection and the one or more boosting injections. A heterologous prime-boost vaccination uses a vaccine comprising the same immunogen for both the priming injection and the one or more boosting injections but different vectors for the priming injection and the one or more boosting injections. In a specific non-limiting example, a homologous prime-boost vaccination may use a modified vaccinia Ankara (MVA) vector comprising nucleic acids expressing PSA and TRICOM for both the priming injection and the one or more boosting injections. In contrast, a heterologous prime-boost vaccination may use an MVA vector comprising nucleic acids expressing PSA and TRICOM for the priming injection and a fowlpox vector comprising nucleic acids expressing a different antigen, such as Brachyury, and TRICOM for the one or more boosting injections. Heterologous prime-boost vaccination also encompasses various combinations such as, for example, use of a plasmid encoding an immunogen in the priming injection and use of a poxvirus vector encoding the same immunogen in the one or more boosting injections, or use of a recombinant protein immunogen in the priming injection and use of a plasmid or poxvirus vector encoding the same protein immunogen in the one or more boosting injections.

Prognosis: The probable course or outcome of a disease process. In several examples, the prognosis of a subject with cancer can indicate the likelihood of survival and/or the likelihood of metastasis. The prognosis of a subject with cancer can indicate the likelihood that the subject will survive for a period of time, such as about one, about two, about three, about four, about five or about ten years. The prognosis of a subject with cancer can also indicate the likelihood of a cure, of the likelihood that the subject will remain disease-free following treatment for a period of time, such as about one, about two, about three, about four, about five or about ten years.

Prostate Cancer: A malignant tumor, generally of glandular origin, of the prostate. Prostate cancers include adenocarcinomas and small cell carcinomas. Many prostate cancers express prostate specific antigen (PSA).

Prostate Specific Antigen (PSA): A glycoprotein manufactured almost exclusively by the prostate, and also known as kallikrein III, seminin, semenogelase, γ-seminoprotein and P-30 antigen. PSA is a serine protease, produced by normal prostatic tissue, and secreted exclusively by the epithelial cells lining prostatic acini and ducts. Prostate specific antigen can be detected at low levels in the sera of healthy males without clinical evidence of prostate cancer. However, during neoplastic states, circulating levels of this antigen increase dramatically, correlating with the clinical stage of the disease. Prostate specific antigen is used as a marker for prostate cancer.

Exemplary PSA nucleic acid and amino acid sequences can be found on GENBANK®, for example at Accession Nos. AAA58802 and M27274 as available Dec. 1, 2010, are incorporated herein by reference in their entirety.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Quantitating: Determining or measuring a quantity (such as a relative quantity) of a molecule or the activity of a molecule, such as the quantity of sCD27 present in a sample.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sample: A biological sample obtained from a subject, such as a human or other primate or mammal, which contains for example nucleic acids and/or proteins. As used herein, biological samples include all clinical samples useful for detection of sCD27 in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In particular embodiments, the biological sample is obtained from a subject, such as in the form of a blood sample, such as serum sample.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene* 73: 237-244, 1988; Higgins & Sharp CABIOS 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Specific binding agent: An agent that binds substantially only to a defined target. In some embodiments, a specific binding agent is an antibody that specifically binds sCD27 or a functional fragment thereof.

The term "specifically binds" refers to the preferential association of an antibody or other ligand, in whole or part, with an antigen. It is, of course, recognized that a certain degree of non-specific interaction may occur between a molecule and a non-target antigen. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue expressing the target epitope as compared to a cell or tissue lacking this epitope. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

T-cell: A white blood cell critical to the immune response. T-cells include, but are not limited to, CD4$^+$ T-cells and CD8$^+$ T-cells. A CD4$^+$ T lymphocyte is an immune cell that carries a marker on its surface known as "cluster of differentiation 4" (CD4). These cells, also known as helper T-cells, help orchestrate the immune response, including antibody responses as well as killer T-cell responses. CD8$^+$ T-cells carry the "cluster of differentiation 8" (CD8) marker. In one embodiment, a CD8 T-cell is a cytotoxic T lymphocyte. In another embodiment, a CD8 cell is a suppressor T-cell.

TRICOM: A Triad of COstimlatory Molecules consisting of B7-1 (also known as CD80), intracellular adhesion molecule-1 (ICAM-1, also known as CD54) and lymphocyte function-associated antigen-3 (LFA-3, also known as CD58), commonly included in recombinant viral vectors (e.g., poxviral vectors) expressing a specific antigen in order to increase the antigen-specific immune response. The individual components of TRICOM can be under the control of the same or different promoters, and can be provided on the same vector with the specific antigen or on a separate vector. Exemplary vectors are disclosed, for example, in Hodge et al., "A Triad of Costimulatory Molecules Synergize to Amplify T-Cell Activation," *Cancer Res.* 59:5800-5807 (1999) and U.S. Pat. No. 7,211,432 B2, both of which are incorporated herein by reference.

Tumor or cancer: The product of neoplasia is a neoplasm (a tumor or cancer), which is an abnormal growth of tissue that results from excessive cell division. A tumor that does not metastasize is referred to as "benign." A tumor that invades the surrounding tissue and/or can metastasize is referred to as "malignant." Neoplasia is one example of a proliferative disorder. A solid tumor is an abnormal mass of tissue that usually does not contain cysts or liquid areas. A solid tumor is a cancer of body tissues other than blood, bone marrow, or the lymphatic system, thus for the purposes of this disclosure cancers of the blood, such as leukemias and lymphomas are not solid tumors.

Examples of solid cancers, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (such as adenocarcinoma), lung cancers, gynecological cancers (such as, cancers of the uterus (e.g., endometrial carcinoma), cervix (e.g., cervical carcinoma, pre-tumor cervical dysplasia), ovaries (e.g., ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma), embryonal rhabdomyosarcoma, and fallopian tubes (e.g., carcinoma), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, liver cancer, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma), and skin cancer (such as melanoma and non-melanoma).

II. Description of Several Embodiments

A. Introduction

Soluble receptors of cytokines and growth factors have been investigated in the past two decades. These studies suggest that the majority of soluble receptors compete with their membrane-bound counterparts for ligands and thus act antagonistically; very few were found to be agonistic. Currently, there is no definitive hypothesis regarding the immunological role of the soluble costimulatory receptor CD27. However, the CD27 signaling pathway appears to be associated with the CF40-CD40L signal transduction pathway, since blockage of CD27-CD70 signaling abrogated the antitumor effect induced by agonistic anti-CD40 mAb in a mouse study.

Previous studies have demonstrated that the interaction between CD27 and its ligand, CD70, plays a role in providing costimulation for prolonged lymphocyte survival, enhanced T-cell proliferation, and memory-cell formation. CD27 is a 55-kD type I transmembrane protein and TNF receptor that is expressed on subsets of T, B, natural killer (NK), and hematopoietic progenitor cells. CD27 controls the activity of these cells by engaging with CD70, which is transiently expressed by cells of the immune system upon activation. Other co-stimulatory molecules do not appear to completely compensate for a lack of CD27 ligation with CD70. Evidence also suggests that the ability of anti-CD40 antibody to promote effective CD8+ T-cell antitumor responses is critically dependent on CD27 co-stimulation. Data from murine studies indicate that CD27 co-stimulation induces Th1-cell formation. Studies in humans also show that CD27 signaling in naive CD4+ T-cells promotes IL-12-induced Th1-cell development. Recent studies have demonstrated that the expression of CD27 and CD70 on infused CD8+ tumor infiltrating lymphocytes (TILs) was associated with anti-tumor effects in a melanoma adoptive T-cell transfer clinical trial.

In this disclosure it is demonstrated that sCD27 is preferentially derived from activated CD4+ T cells. Adding sCD27 to stimulated peripheral blood mononuclear cells increases T-cell activation and proliferation, and is associated with the immunological synapse-related proteins myosin IIA, HMGB1, and the TCR V chain. The pool of serum sCD27 was shown to be greater in healthy donors than in subjects with cancer. In addition, subjects with metastatic cancer treated with immunotherapy showed a significant increase in the serum sCD27-pool post-therapy, and there was an association between enhanced sCD27-pool post-therapy and overall survival.

CD27-CD70 interaction is part of the regulation of cellular immune response. A soluble form of CD27 (sCD27) can be produced by T-cells upon activation. As disclosed herein, the functionality of sCD27 in T-cell activation and its association with clinical outcome after the vaccination of cancer subjects was determined. The production of sCD27 is shown to depend on both TCR and CD70 engagement and that CD4+ memory T-cells produce more sCD27 per cell upon activation than other CD3+ cell types. The pool of sCD27 in serum was shown to be greater in healthy donors than in gender- and age-matched prostate cancer subjects. There was a statistical correlation between increased serum sCD27 (post-three monthly vaccinations vs. pre-vaccination) and overall survival in two different prostate cancer vaccine clinical trials. A significant enhancement of serum levels of sCD27 was also observed in a trial of prostate cancer subjects treated with PSA-TRICOM plus an anti-CTLA-4 monoclonal antibody; the increase was antibody dose dependent. In vitro results also demonstrated that sCD27 can increase T-cell proliferation and activation by enhancing CD25, CD70 and 4-IBB on CD8+ T-cells, and CD40L on CD4+ T-cells; sCD27 also enhanced the production of soluble CD40L production on CD4+ T-cells in vitro. These results indicate that the assay for sCD27 in serum is useful in defining those subjects most suited for cancer vaccine clinical trials, and those subjects who are responding to vaccine therapy, early in the vaccination cycle, vs. those subjects who should go on to receive other therapies. These results also demonstrate that sCD27 protein can be used to stimulate a subject's immune system.

B. Methods for Diagnosing or Predicting

Disclosed are methods for diagnosing or predicting a predisposition to develop a solid tumor (for example, colorectal cancer, breast cancer or prostate cancer) in a subject, such as a human subject. Also disclosed are methods for determining or monitoring the effectiveness of one or more therapeutic agents.

In some embodiments, the methods include obtaining a biological sample from the subject, for example a sample of blood or a blood fraction, such as serum. The amount of sCD27 present in the biological sample (for example, a serum sample) is detected and compared to a control, such as a control indicative of a similar sample obtained from a subject who does not have a solid tumor (such as colorectal cancer, breast cancer or prostate cancer) and/or does not have any predisposition for developing a solid tumor (such as colorectal cancer or prostate cancer) or a reference value indicative of the basal level of sCD27 present in a serum sample in a subject that does not have a solid tumor (such as colorectal cancer, breast cancer or prostate cancer) and does not have any predisposition for developing a solid tumor (such as colorectal cancer, breast cancer or prostate cancer)).

In some examples, the amount of sCD27 in a sample being tested is compared to a control. In some examples, the control is the amount of sCD27 in a sample obtained from the subject from an earlier time point. In some examples, a control is a value indicative of the basal amount of sCD27. In some examples, the control is a statistical value, for example measured from multiple control samples.

If there is decrease in the amount of sCD27 detected in the biological sample, such as a serum sample, relative to the control (such as an amount of sCD27 in a normal biological sample, for example a reference value or range of values representing the expected sCD27 levels in a serum sample), the subject is diagnosed or predicted to have a predisposition to developing cancer. For example, a decrease of at least 10%, at least 20%, at least 30%, at least 50%, at least 75%, at least 80%, at least 90%, at least 100%, at least 200% or even at least 500%, relative to the control, indicates that the subject (such as a human subject) has a predisposition to developing a solid tumor, such as colorectal cancer, breast cancer or prostate cancer, respectively.

Conversely, an increase or maintenance in the amount of sCD27 detected in the biological sample, such as a serum sample, relative to the control (such as an amount of sCD27 in a normal biological sample, for example a reference value or range of values representing the expected sCD27 levels in a serum sample) indicates that the subject does not have a predisposition to develop a solid tumor, such as colorectal cancer, breast cancer or prostate cancer.

Also disclosed are methods for determining a subject's suitability for immunotherapy. The amount of sCD27 present in the serum sample is detected and compared with a control value indicative of the basal level of sCD27 present in the serum of a healthy subject, for example a statistical value, for example measured from multiple control samples, or a subject that does not have a solid tumor. A reduction of the amount of sCD27 in the serum sample obtained from the subject relative to the control value indicates that the subject would not benefit from immunotherapy. In such a situation, it is believed that such a subject would not benefit from immunotherapy because their immune system is compromised in some way that is manifested by a reduction of the serum levels of sCD27 relative to normal level. In some examples, it might be possible to augment the subject's immune system so that the subject would benefit from immunotherapy, for example by administering an immunostimulatory agent, such as sCD27, to the subject, for example as described in Section C below. In some examples, the subject that is being tested for suitability for immunotherapy has been diagnosed with a solid tumor, such as a colorectal cancer tumor or a prostate cancer tumor. Optionally, the subject is administered a therapeutic agent.

The disclosed methods can also be used to select a subject for treatment for a solid tumor, for example treatment with a therapeutic agent. In some embodiments, the methods including administering to the subject the therapeutic agent, such as an anti-cancer vaccine. The anticancer vaccine can be, for example, rV-PSA, rV-B7.1, rF-PSA, rV-PSA-B7.1-ICAM-1-LFA-3, rF-PSA-TRICOM, PROSTVAC®, or a combination thereof, such as, for example, for the treatment of prostate cancer. The anticancer vaccine can be a poxviral anticancer vaccine, for example, an *orthopox* virus, an avipox virus, a capripox virus, a suipox virus, a raccoon pox virus, a rabbit pox virus, or a vaccinia virus, such as a modified vaccinia virus Ankara ("MVA") or an MVA-Bavarian Nordic ("MVA-BN"), encoding protein or peptide that includes cancer specific CD4+ and/or CD8+ T cells and optionally TRICOM. In some examples, the treatment selected is administering to the subject an anti-cancer antibody, for example the anti-CTLA4 antibody, such as ipilimumab, for example for the treatment of prostate cancer. In some examples, the immunotherapy is administration of an anticancer vaccine, such as rV-PSA, rV-B7.1, rF-PSA, rV-PSA-B7.1-ICAM-1-LFA-3, rF-PSA-TRICOM, PROSTVAC®, and another immunotherapy. In some examples, the immunotherapy is administration of an anti-cancer antibody, for example an anti-CTLA4 antibody, for the treatment of prostate cancer. In further examples the treatment is an anti-CTLA4 antibody, such as ipilimumab, and an anticancer vaccine, such as a vaccine including TRICOM, such as, but not limited to rF-PSA-TRICOM or PROSVAC®.

In some embodiments, the therapeutic agent is a yeast-based immunotherapy composition which can be used to prevent and/or treat cancers. The composition is a yeast-cancer antigen immunotherapeutic composition comprising: (a) a yeast vehicle; and (b) a cancer antigen comprising one or peptides or proteins and/or immunogenic domain(s) thereof. The protein, peptide, or immunogenic domain thereof is most typically expressed as a recombinant protein by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more proteins, peptides, or immunogenic domains thereof are loaded into a yeast vehicle or otherwise complexed with, attached to, mixed with or administered with a yeast vehicle.

In yet other examples, the immunotherapy is a non-pox non-yeast vector encoding a protein or peptide that can be used to induce cancer-specific T cells, such as CD4+ and/or CD8+ cancer-specific T cells. In some non-limiting examples, the vector is an alphavirus, a lentiviurs, an adenovirus, a measles virus or a poliovirus vector. In additional embodiments, the immunotherapy is host cells transformed with these vectors, such as *Salmonella* and *Listeria* host cells. The immunotherapy can also be a liposome including a protein or peptide that includes cancer specific T cells or a nucleic acid encoding a protein or peptide that induces cancer-specific T cells.

The methods can further include administering a therapeutically effective amount of other agents to the subject. In certain embodiments, the second agent is selected from the group consisting of cytokines, chemotherapeutics, and radiotherapeutics. In certain embodiments, the second agent is a cytokine. In certain embodiments, the cytokine is selected from the group consisting of interleukin (IL)-2, IL-3, IL-6, IL-10, IL-12, IL-15, GM-CSF, interferon (IFN)-α, IFN-β, IFN-γ, and IFN-ω. In certain embodiments, the second agent is a chemotherapeutic. In certain embodiments, the chemotherapeutic is selected from the group consisting of alkylating agents, antimetabolites, hormone antagonists, targeted therapeutics, and miscellaneous agents. In certain embodiments, the chemotherapeutic is an alkylating agent. In certain embodiments, the alkylating agent is selected from the group consisting of nitrogen mustards, alkyl sulfonates, and nitrosoureas. In certain embodiments, the chemotherapeutic is an antimetabolite. In certain embodiments, the antimetabolite is selected from the group consisting of folic acid analogs, pyrimidine analogs, purine analogs, and topoisomerase inhibitors. In certain embodiments, the chemotherapeutic is a natural product. In certain embodiments, the natural product is selected from the group consisting of vinca alkaloids, epipodophyllotoxins, antibiotics, and enzymes. In certain embodiments, the chemotherapeutic is a hormone or hormone antagonist. In certain embodiments, the hormone or hormone antagonist is selected from the group consisting of adrenocorticosteroids, progestins, estrogens, antiestrogens, and androgens. In certain embodiments, the chemotherapeutic agent is a targeted therapeutic. In certain embodiments, the targeted therapeutic is selected from the group consisting of selective estrogen receptor modulators (SERMs), aromatase inhibitors, topoisomerase inhibitors, tyrosine kinase inhibitors, serine/threonine kinase inhibitors, histone deacetylase (HDAC) inhibitors, retinoid receptor activators, apoptosis stimulators, angiogenesis inhibitors, and poly (ADP-ribose) polymerase (PARP) inhibitors. In certain embodiments, the chemotherapeutic is a miscellaneous agent. In certain embodiments, the miscellaneous agent is selected from the group consisting of platinum coordination complexes, substituted ureas, methyl hydrazine derivatives, and adrenocortical suppressants.

The disclosed methods are particularly useful in monitoring the effectiveness of a treatment, such as an immune stimulatory treatment, for example the effectiveness of a treatment for a solid tumor in a subject, for example prostate cancer treatment, breast cancer treatment or a colorectal cancer treatment, such as any of the treatments disclosed above. Typically, the disclosed methods are used to compare the amount of sCD27 present in the serum of a subject before and after treatment, although they could also be monitored during treatment, for example prolonged treatment. The method can be used to monitor the effectiveness of a treatment after one or more administrations of a therapeutic agent, such as 1, 2, 3, 4, 5, 6, 7, 8, 9 or 10 administrations of one or more therapeutic agents. In specific non-limiting examples, the method can be used to monitor the effectiveness of more than 2, 3, 4, 5, 6, 7, 8, 9, or 10 administrations of one or more therapeutic agents, such as, but not limited to, an anticancer vaccine, such as rV-PSA, rV-B7.1, rF-PSA, rV-PSA-B7.1-ICAM-1-LFA-3, rF-PSA-TRICOM, PROSTVAC®, and/or an immunotherapy, such as an anti-CTLA4 antibody, for example ipilimumab. The method can monitor the effectiveness of a prime boost strategy.

In one specific non-limiting example, the anticancer vaccine is PROSTVAC®, a poxviral vector which encodes prostate-specific antigen and three costimulatory molecules known as TRICOM (B7.1, ICAM-1, and LFA-3). Optionally, PROSTVAC® is combined with one or more additional agents, such as any of the agents disclosed above. In additional non-limiting examples, the effectiveness of one or more administrations of PROSTVAC and ipilmumab is monitored using the methods disclosed herein.

In some embodiments, the methods include quantitating an amount of sCD27 present in a first serum sample from the subject following treatment with the one or more therapeutic agents. A statistically significant increase the amount of sCD27 detected is compared with a control value, wherein the control value is a level of sCD27 present in a second serum sample from the subject prior to the treatment with the therapeutic agent. The detection of the statistically significant increase in the amount of sCD27 in the first serum sample as compared to the amount of sCD27 in the second sample indicates that the treatment is effective for treating the subject, wherein the subject has a solid tumor. In specific non-limiting examples, quantitating an amount of sCD27 includes contacting the sample with an antibody that specifically binds sCD27 under conditions sufficient for the antibody to form an immune complex with sCD27 and determining the quantity of the immune complex.

In some embodiments, the methods can include detecting an amount of sCD27 in a biological sample (such as a serum sample) obtained from a subject that is undergoing a treatment for a solid tumor, such as colorectal cancer, breast cancer or prostate cancer. In some embodiments, methods of monitoring the effectiveness of a treatment or even monitoring disease progression in a subject involve detecting the amount of sCD27 present in a first sample, such as a first serum sample, obtained from a subject at a first time point and comparing that to the amount sCD27 present in a second sample, such as a second serum sample, obtained from a subject at a second time point, for example a later time point, which could be separated by days, weeks months, or even years. A decrease in the amount of sCD27 in the second biological sample relative to the amount of sCD27 expressed in the first biological sample indicates that the subject is not responding to the treatment or that the disease is progressing. For example, a reduction of at least 10%, at least 20%, at least 30%, at least 50%, at least 75%, at least 80%, at least 90%, at least 95%, at least 98% or even at least 99%, indicates that the subject (such as a human subject being treated for cancer) is not responding to the treatment or that the disease is progressing.

Conversely an increase in or maintenance of the amount of sCD27 expressed in the second biological sample relative to the amount of sCD27 expressed in the first biological sample indicates that the subject is responding to the treatment or that the disease is not progressing. For example, an increase of at least 10%, at least 20%, at least 30%, at least 50%, at least 75%, at least 80%, at least 90%, at least 100%, at least 200% or even at least 500%, indicates that the subject is responding to the treatment or that the disease is not progressing.

In specific non-limiting examples, the treatment is a treatment for a solid tumor, for example treatment that includes an anticancer vaccine, such as rV-PSA, rV-B7.1, rF-PSA, rV-PSA-B7.1-ICAM-1-LFA-3, rF-PSA-TRICOM or a combination thereof for the treatment of prostate cancer. The treatment can be an anticancer vaccine, such as a poxviral anticancer vaccine, for example, an *orthopox* virus, an avipox virus, a capripox virus, a suipox virus, a raccoon pox virus, a rabbit pox virus, or a vaccinia virus, such as a modified vaccinia virus Ankara ("MVA") or an MVA-Bavarian Nordic ("MVA-BN"), encoding a tumor antigen and optionally TRICOM. In some examples, the treatment includes an anti-cancer antibody, for example the anti-CTLA4 antibody, for the treatment of prostate cancer. In another example, the treatment is ipilimumab. In further examples the treatment is an anti-CTLA4 antibody, such as ipilimumab, and an anticancer vaccine, such as a vaccine including TRICOM, such as, but not limited to rF-PSA-TRICOM or PROSVAC®. The effectiveness of multiple administrations, such as 2, 3, 4, 5, 6, 7, 8, 9, 10 or more administrations, can be monitored using the methods disclosed herein.

Thus, in additional non-limiting examples, the method is used to monitor the effectiveness of administration of a therapeutic agent that is an anticancer vaccine, such as a vector, for example a poxviral vector, encoding TRICOM and any cancer antigen. The poxviral vector can be an *orthopox* virus, an avipox virus, a capripox virus, a suipox virus, a raccoon pox virus, a rabbit pox virus, or a vaccinia virus, such as a modified vaccinia virus Ankara ("MVA") or an MVA-Bavarian Nordic ("MVA-BN") encoding a tumor antigen and optionally TRICOM. The antigen can be a prostate cancer antigen, such as, but not limited to, PSA. In further examples the therapeutic agent is an immunotherapy, such as an anti-CTLA-4 antibody, for example ipilimumab, and an anticancer vaccine, such as a vaccine including TRICOM, such as, but not limited to rF-PSA-TRICOM or PROSVAC®. The effectiveness of 2, 3, 4, 5, 6, 7, 8, 9, 10 or more administrations of the therapeutic agent can be monitored using the methods disclosed herein. In specific non-limiting examples, the effectiveness of more than 3, such as 4, 5, 6, 7, 8, 9 or 10 administrations is determined using the methods disclosed herein.

In some embodiments of the disclosed methods, determining the amount of sCD27 expressed in a biological sample includes determining the amount of sCD27 protein, such as a sCD27 protein with an amino acid sequence at least 80% identical, such as at least 85% identical, at least 90% identical, at least 95% identical, as at least 98% identical, or even 100% identical to SEQ ID NO. 1 or a fragment thereof, for example, a biologically active fragment. Methods of determining if a fragment of sCD27 is biologically active are routine in the art given the present disclosure, for example the biological activity of any fragment can be determined by the ability of the fragment to stimulate CD8+ positive T-cells as described in the Examples Section below. In one specific embodiments, a biologically active fragment of sCD27 protein includes amino acid residues 1 through 189 of the CD27 protein set forth as SEQ ID NO: 1. In other embodiments, a biologically active fragment of CD27 is at most 25, 50, 75, 100, 125, 150 or 175 consecutive amino acids of amino acids 1-189 of SEQ ID NO: 1.

It is contemplated that sCD27 can contain one or more conservative amino acid substitutions, for example polymorphisms present in the population. "Conservative" amino acid substitutions are those substitutions that do not substantially affect or decrease an activity or antigenicity of sCD27 disclosed herein and can include at most about 1, at most about 2, at most about 5, and at most about 10, or at most about 15 conservative substitutions and specifically bind an antibody that binds the original sCD27 such as set forth in GENBANK® Accession No. NP_001233 as available Dec. 3, 2010, which is incorporated herein by reference in its entirety and given as SEQ ID NO: 1. Conservative variations also include the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

sCD27 protein can be detected and the amount of sCD27 protein present in the biological sample can be detected through novel epitopes recognized by polyclonal and/or monoclonal antibodies used in ELISA assays, immunoblot assays, flow cytometric assays, immunohistochemical assays, radioimmuno assays, Western blot assays, immunofluorescent assays, chemiluminescent assays and other polypeptide detection strategies (Wong et al., *Cancer Res.,* 46: 6029-6033, 1986; Luwor et al., *Cancer Res.,* 61: 5355-5361, 2001; Mishima et al., *Cancer Res.,* 61: 5349-5354, 2001; Ijaz et al., *J. Med. Virol.,* 63: 210-216, 2001). Generally these methods utilize antibodies, such as monoclonal or polyclonal antibodies.

Generally, immunoassays for sCD27 protein typically include incubating a biological sample in the presence of antibody or other sCD27 specific binding agent, and detecting the bound antibody or binding agent by any of a number of techniques well known in the art. The biological sample can be a blood sample or a fraction thereof, such as a serum sample. In specific embodiments, a biological sample is a serum sample obtained from a subject.

In some embodiments, the amount of sCD27 protein present in the biological sample is detected using a sCD27 specific binding agent, such as an antibody or ligand for sCD27, such as CD70, which optionally can be detectably labeled. In some embodiments, the specific binding agent is an antibody, such as a polyclonal or monoclonal antibody, that specifically binds sCD27. In other embodiments, the specific binding agent is CD70. Thus, in certain embodiments, determining the amount of sCD27 in a biological sample includes contacting a biological sample from the subject with a sCD27 specific binding agent (such as an antibody that specifically binds sCD27 or CD70), detecting whether the binding agent is bound by the sample, and thereby measuring the amount of sCD27 present in the sample.

In one embodiment, the specific binding agent is a monoclonal or polyclonal antibody that specifically binds the sCD27. An antibody that specifically binds sCD27 binds with an affinity constant of at least $10^7$ $M^{-1}$, such as at least $10^8$ $M^{-1}$ at least $5\times10^8$ $M^{-1}$ or at least $10^9$ $M^{-1}$. All of these antibodies are of use in the methods disclosed herein.

The preparation of polyclonal antibodies is well known to those skilled in the art. See, for example, Green et al., "Production of Polyclonal Antisera," in: *Immunochemical Protocols* pages 1-5, Manson, ed., Humana Press 1992; Coligan et al., "Production of Polyclonal Antisera in Rabbits, Rats, Mice and Hamsters," in: *Current Protocols in Immunology*, section 2.4.1, 1992.

The preparation of monoclonal antibodies likewise is known. See, for example, Kohler & Milstein, *Nature* 256: 495, 1975; Coligan et al., sections 2.5.1-2.6.7; and Harlow et al., in: *Antibodies: a Laboratory Manual*, page 726, Cold Spring Harbor Pub., 1988. Briefly, monoclonal antibodies can be obtained by injecting mice with a composition including an antigen or a cell of interest, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Methods of in vitro and in vivo multiplication of monoclonal antibodies have also been described. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors.

Optionally, the animals are primed with a hydrocarbon, especially oils such as pristane (tetramethylpentadecane) prior to injection. After one to three weeks, the desired monoclonal antibody is recovered from the body fluid of the animal.

Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. U.S.A.* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. U.S.A.* 9:4285, 1992; Sandhu, *Crit. Rev. Biotech.* 12:437, 1992; and Singer et al., *J. Immunol.* 150:2844, 1993.

Antibodies include intact molecules as well as functional fragments thereof, such as Fab, F(ab')$_2$, and Fv which are capable of binding the epitopic determinant. These antibody fragments retain some ability to selectively bind with their antigen. Methods of making these fragments are known in the art. (See for example, Harlow and Lane, *Antibodies: A Laboratory Manual*, Cold Spring Harbor Laboratory, New York, 1988).

In some examples, the biological sample can be brought in contact with and immobilized onto a solid phase support or carrier such as nitrocellulose, or other solid support which is capable of immobilizing soluble proteins. The support may then be washed with suitable buffers followed by treatment with the antibody that binds sCD27 protein, or another sCD27 binding agent, such as CD70. The solid phase support can then be washed with the buffer a second time to remove unbound antibody. If the binding agent, such as the antibody, is directly labeled, the amount of bound label on solid support can then be detected by conventional means. If the binding agent, such as the antibody, is unlabeled, a labeled second antibody, which detects the binding agent that specifically binds sCD27 protein can be used. By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros and magnetite. The nature of the carrier can be either soluble to some extent or insoluble for the purposes of the present disclosure. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet or test strip.

In one embodiment, sCD27 proteins are isolated from a biological sample, such as a serum sample obtained from a subject. In one embodiment, ELISA is utilized to detect the sCD27 protein (see e.g. Voller, "The Enzyme Linked Immunosorbent Assay (ELISA)," *Diagnostic Horizons* 2:1-7, 1978, Microbiological Associates Quarterly Publication, Walkersville, Md.; Voller et al., *J. Clin. Pathol.* 31:507-520, 1978; Butler, *Meth. Enzymol.* 73:482-523, 1981; Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). In this method, an enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

However, detection can also be accomplished using any of a variety of other immunoassays. For example, by radioactively labeling the antibodies or antibody fragments, it is possible to detect fingerprint gene wild-type or mutant peptides through the use of a radioimmunoassay (RIA) (see, for example, Weintraub, *Principles of Radioimmunoassays, Seventh Training Course on Radioligand Assay Techniques*, The Endocrine Society, March, 1986, which is incorporated by reference herein). In another example, a sensitive and specific tandem immunoradiometric assay may be used (see Shen and Tai, *J. Biol. Chem.*, 261:25, 11585-11591, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent compounds for purposes of labeling are luciferin, luciferase and aequorin.

Binding affinity for a target antigen can be measured or determined by standard antibody-antigen assays, such as competitive assays, saturation assays, or immunoassays such as ELISA or RIA. Such assays can be used to determine the dissociation constant of the antibody utilized in the assay. The phrase "dissociation constant" refers to the affinity of an antibody for an antigen. In some embodiments, specificity of binding between an antibody and an antigen exists if the dissociation constant ($K_D=1/K$, where K is the affinity constant) of the antibody is, for example <1 μM, <100 nM, or <0.1 nM. Antibody molecules will typically have a $K_D$ in the lower ranges. $K_D=[Ab-Ag]/[Ab][Ag]$ where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible non-covalent associations such as electrostatic attraction, Van der Waals forces and hydrogen bonds.

Examples of antibodies that specifically bind sCD27 include those available from ABCAM®, for example catalogue numbers ab10456, ab49518, ab75297, ab80777, ab1091, ab28064, ab30366, ab36417 and ab69773, ab89258, and ab95597 or Santa Cruz Biotechnology® for example catalogue numbers sc-66200, sc-70607, sc-70606, sc-25289, sc-1739, sc-20923, sc-51535, sc-1743, sc-19653, sc-1740, sc-53662, and sc-65271. One skilled in the art will appreciate that there are other commercial sources for antibodies to sCD27.

The presence of a sCD27 can be detected with multiple specific binding agents, such as one, two, three, or more specific binding agents. Thus, the methods can utilize more than one antibody. In some embodiments, one of the antibodies is attached to a solid support, such as a multiwell plate (such as a microtiter plate), bead, membrane or the like. In practice, microtiter plates may conveniently be utilized as the solid phase. The surfaces may be prepared in advance, stored, and shipped to another location(s). However, antibody reactions also can be conducted in a liquid phase.

Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions that can be conjugated to antibodies for use as diagnostics according to the present invention. The particular label used will depend upon the type of immunoassay.

The enzymes that can be conjugated to the antibodies include, but are not limited to, alkaline phosphatase, peroxidase, urease, β-galactosidase, horse radish peroxidase, lysozyme, glucose-6-phosphate dehydrogenase, and acetylcholinesterase. The fluorochromes that can be conjugated to the antibodies include, but are not limited to, fluorescein and its derivatives, rhodamine and its derivatives, dansyl and umbelliferone; rhodamine and its derivatives, dansyl and umbelliferone; chemiluminescers such as luciferase and 2,3-dihydro-phthalazinediones; isothiocyanate, tetramethylrhodamine isothiocyanate, phycoerythrin, allophycocyanins, Texas Red and chemiluminescers such as luciferase and 2,3-dihydro-phthalazinediones, For additional fluorochromes that can be conjugated to antibodies see Haugland, R. P., *Molecular Probes: Handbook of Fluorescent Probes and Research Chemicals* (1992-1994). The metal compounds that can be conjugated to the antibodies include, but are not limited to, ferritin, colloidal gold, silver, and particularly colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}$Tc), $^{125}$I, $^{131}$I, $^{14}$C, $^{3}$H $^{32}$P and $^{35}$S.

The antibodies or other specific binding agents can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described, for example, in IMMUNOASSAY: A PRACTICAL GUIDE (1987, Chan (Ed.), Academic Press, Inc. Orlando, Fla.).

Any method known to those of skill in the art can be used to detect and quantify sCD27. Thus, in additional embodiments, a spectrometric method is utilized. Spectrometric methods include mass spectrometry, nuclear magnetic resonance spectrometry, and combinations thereof. In one example, mass spectrometry is used to detect the presence of sCD27 in a biological sample, such as a blood sample, a serum sample, or a plasma sample (see for example, Stemmann, et al., *Cell Dec.* 14; 107(6):715-26, 2001; Zhukov et al., "From Isolation to Identification: Using Surface Plasmon Resonance-Mass Spectrometry in Proteomics, PharmaGenomics, March/April 2002, available on the PharmaGenomics website on the internet).

sCD27 protein also can be detected by mass spectrometry assays for example coupled to immunoaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of proteins separated by two-dimensional polyacrylamide gel electrophoresis (2D-PAGE) (Kiernan et al., *Anal. Biochem.*, 301: 49-56, 2002; Poutanen et al., *Mass Spectrom.*, 15: 1685-1692, 2001).

This disclosure also provides integrated systems for high-throughput determination of sCD27 presence and or amount. The systems typically include a robotic armature that transfers fluid from a source to a destination, a controller that controls the robotic armature, a tag detector, a data storage unit that records tag detection, and an assay component such as a microtiter dish comprising a well having a reaction mixture. A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous assays.

Optionally, optical images can viewed (and, if desired, recorded for future analysis) by a camera or other recording device (for example, a photodiode and data storage device) and are optionally further processed in any of the embodiments herein, such as by digitalizing, storing, and analyzing the image on a computer. A variety of commercially available peripheral equipment and software is available for digitizing, storing and analyzing a digitized video or digitized optical image, e.g., using PC (Intelx86 or Pentium chip-compatible DOS™, OS2™ WINDOWS™ WINDOWS NT™ or WINDOWS95™ based computers), MACINTOSH™, or UNIX based (for example, a SUN™, a SGI™, or other work station) computers.

C. Therapeutic Methods and Pharmaceutical Compositions

The soluble CD27 (sCD27) polypeptides disclosed herein or functional fragments thereof, such as amino acids 1 to 189 of sCD27 for example as set forth as SEQ ID NO: 1, or nucleic acids encoding sCD27 polypeptides, for example as set forth as SEQ ID NO: 2, can be used to stimulate the immune system of a subject, for example when administered to the subject, such as in a therapeutically effective amount. In some embodiments, the sCD27 polypeptides contain an amino acid sequence that is at least 95% identical to the amino acid sequence set forth as residues 1-189 of SEQ ID NO: 1, such as at least 95%, at least 96%, at least 97%, at least 98%, at least 99%, or 100% identical to the amino acid sequence set forth as residues 1-189 of SEQ ID NO: 1. It is contemplated by this disclosure that other functional fragments can be used in the disclosed methods. Methods of determining the amino aid sequence of a functional fragment of sCD27 are discussed in the previous section.

In some embodiments, the methods can include selecting a subject in need of treatment. In several examples, the methods include selecting a subject with a compromised or reduced immune system, for example the subject has reduced levels of sCD27 as compared to a subject without a compromised or reduced immune system. In some examples, in addition to sCD27polypeptides, functional fragments thereof or nucleic acids encoding sCD27 polypeptides, the subject is also administered a therapeutically effective amount of interleukin 2 (IL-2). In some examples, the subject's stimulation includes T-cell activation, for example CD8+ T-cell activation.

In some embodiments, the subject does not have an autoimmune disorder, such as systemic lupus erythematosus. In some embodiments, the subject does not have Waldenstroms macroglobulinemia.

In some examples, the subject has been diagnosed with a solid tumor, for example a colorectal cancer tumor, or a prostate cancer tumor. Thus, the disclosed method can be a method for treating cancer, for example a solid tumor, such as colorectal cancer tumor, or a prostate cancer tumor. The methods can include selecting a subject in need of treatment. In several examples, the methods include selecting a subject with a solid tumor, for example a colorectal cancer tumor, or a prostate cancer tumor. Such methods include administering to a subject with a solid tumor a therapeutically effective amount of a sCD27 polypeptide, functional fragments thereof or nucleic acids encoding sCD27 polypeptides in order to generate an immune response, for example to increase the subject's ability, through immune system enhancement, to fight the cancer. In some embodiments, a subject is selected that has a solid tumor, such as colorectal cancer or prostate. In some embodiments, the subject does not have a cancer of hematopoietic origin. In some embodiments, the subject is also administered an anticancer vaccine. In some examples, the anticancer vaccine is an anticancer vaccine specific for prostate cancer, such as rV-PSA, rV-B7.1, rF-PSA, rV-PSA-B7.1-ICAM-1-LFA-3, rF-PSA-TRICOM or a combination thereof. In some embodiments, the subject is also administered an anti-cancer antibody, for example an antibody that has been designed to specially bind a tumor antigen. Examples of tumor antigens include, but are not limited to, RAGE-1, tyrosinase, MAGE-1, MAGE-2, NY-ESO-1, Melan-A/MART-1, glycoprotein (gp) 75, gp100, beta-catenin, preferentially expressed antigen of melanoma (PRAME), MUM-1, Wilms tumor (WT)-1, carcinoembryonic antigen (CEA), and PR-1. Additional tumor antigens are known in the art (for example see Novellino et al., *Cancer Immunol. Immunother.* 54(3):187-207, 2005) and are described below. The tumor antigen can be any tumor-associated antigen, which are well known in the art and include, for example, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, macrophage colony stimulating factor, prostase, prostate-specific antigen (PSA), PAP, NY-ESO-1, LAGE-1a, p53, prostein, PSMA, Her2/neu, survivin and telomerase, prostate-carcinoma tumor antigen-1, MAGE, ELF2M, neutrophil elastase, ephrinB2, CD22, insulin growth factor (IGF)-I, IGF-II, IGF-I receptor and mesothelin. A list of selected tumor antigens and their associated tumors are shown below in Table 1.

TABLE 1

Exemplary tumors and their tumor antigens

| Tumor | Tumor Associated Target Antigens |
|---|---|
| Malignant melanoma | MAGE, MART, Tyrosinase, PRAME GP100 |
| Breast cancer | WT1, Herceptin, epithelial tumor antigen (ETA) |
| Lung cancer | WT1 |
| Ovarian cancer | CA-125 |
| Prostate cancer | PSA |
| Pancreatic cancer | CA19-9, RCAS1 |
| Colon cancer | CEA |
| Cervical Cancer | SCC, CA125, CEA, Cytokeratins (TPA, TPS, Cyfra21-1) |
| Renal cell carcinoma (RCC) | Fibroblast growth factor 5 |
| Germ cell tumors | AFP |

In a specific example a tumor antigen is CTLA4 and the subject is administered a therapeutically effective amount of anti-CTLA4 antibody.

A sCD27 polypeptide, or functional fragment thereof can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, intraperitoneal or intravenous injection, but even oral, nasal, transdermal or anal administration is contemplated. In one embodiment, administration is by subcutaneous or intramuscular injection. To extend the time during which the peptide or protein is available to stimulate the immune system, the peptide or protein can be provided as an implant, an oily injection, or as a particulate system. The particulate system can be a microparticle, a microcapsule, a microsphere, a nanocapsule, or similar particle. (see, e.g., Banga, supra).

In one specific, non-limiting example, the sCD27 polypeptide is administered in a manner to direct the immune response to a cellular response (that is, a cytotoxic T lymphocyte (CTL) response), rather than a humoral (antibody) response. Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6(Suppl 1):S61-6; Cao et al., 1998, Stem Cells 16(Suppl 1):251-60;

Kuiper et al., 2000, Adv. Exp. Med. Biol. 465:381-90). These molecules can be administered systemically (or locally) to the host.

Also disclosed are nucleic acid molecules encoding these sCD27 polypeptides. In some embodiments, the nucleic acid molecules include a nucleic acid sequence encoding an amino acid sequence at least 95% identical to the amino acids set forth as residues 1-189 of SEQ ID NO: 1, such as at least 95%, at least 96%, at least 97%, at least 98%, at least 99%, or 100% identical to the amino acids set forth as residues 1-189 of SEQ ID NO: 1. These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

A nucleic acid encoding a sCD27 polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

In the context of the compositions and methods described herein, a nucleic acid sequence that encodes a sCD27 polypeptide, such as described above, is incorporated into a vector capable of expression in a host cell, using established molecular biology procedures. For example nucleic acids, such as cDNAs, that encode sCD27 can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

Exemplary procedures sufficient to guide one of ordinary skill in the art through the production of vector capable of expression in a host cell (such as an adenoviral vector) that includes a polynucleotide sequence that encodes a sCD27 polypeptide can be found for example in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., Wiley & Sons, 1999.

Typically, a polynucleotide sequence encoding a sCD27 polypeptide is operably linked to transcriptional control sequences including, for example a promoter and a polyadenylation signal. A promoter is a polynucleotide sequence recognized by the transcriptional machinery of the host cell (or introduced synthetic machinery) that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are isolated from mammalian genes, including the immunoglobulin heavy chain, immunoglobulin light chain, T-cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, dendritic cell-specific promoters, such as CD11c, macrophage-specific promoters, such as CD68, Langerhans cell-specific promoters, such as Langerin, and promoters specific for keratinocytes, and epithelial cells of the skin and lung.

The promoter can be either inducible or constitutive. An inducible promoter is a promoter which is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2 kb, HSP70, proliferin, tumor necrosis factor, or thyroid stimulating hormone gene promoter.

Typically, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

The polynucleotides encoding a sCD27 polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

Viral vectors can also be prepared encoding the sCD27 polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a sCD27 polypeptide is included in a viral vector. Suitable vectors include retrovirus vectors, *orthopox* vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus, yeast and the like.

It is understood that portions of the nucleic acid sequences encoding sCD27 polypeptides can be deleted as long as the polypeptides are functionally active. For example, it may be desirable to delete one or more amino acids from the N-terminus, C-terminus, or both. Exemplary methods of determining whether a fragment of sCD27 is functional active are given in the Examples below. It is also contemplated that the substitution of residues in the disclosed sCD27 polypeptides can be made, such that the ability of the functionality of the sCD27 polypeptides is maintained.

The sCD27 polypeptides and nucleic acids encoding sCD27 polypeptides can be administered in vitro, ex vivo or in vivo to a cell or subject. Generally, it is desirable to prepare the compositions as pharmaceutical compositions appropriate for the intended application. Accordingly, methods for making a medicament or pharmaceutical composition containing the polypeptides, nucleic acids, adenovirus vectors or adenoviruses described above are included herein. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake of nucleic acids or virus by target cells.

Therapeutic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount of the adenovirus vector or virus dispersed (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the vectors or viruses in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

In some cases the compositions are administered to enhance the immune response, in such applications, the pharmaceutical composition is administered in a therapeutically effective amount. A therapeutically effective amount is a quantity of a composition used to achieve a desired effect in a subject. When administered to a subject, a dosage will generally be used that will achieve target tissue concentrations (for example, in lymphocytes) that has been shown to achieve an in vitro or in vivo effect.

Administration of therapeutic compositions can be by any common route as long as the target tissue (typically, the respiratory tract) is available via that route. This includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. Such pharmaceutical compositions are usually administered as pharmaceutically acceptable compositions that include physiologically acceptable carriers, buffers or other excipients.

The pharmaceutical compositions can also be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well known parameters.

Additional formulations are suitable for oral administration. Oral formulations can include excipients such as, pharmaceutical grades of mannitol, lactose, starch, magnesium stearate, sodium saccharine, cellulose, magnesium carbonate and the like. The compositions (medicaments) typically take the form of solutions, suspensions, aerosols or powders. Exemplary formulations can be found in U.S. Patent publication No. 20020031527, the disclosure of which is incorporated herein by reference. When the route is topical, the form may be a cream, ointment, salve or spray. Exemplary methods for intramuscular, intranasal and topical administration of the adenovirus vectors and adenoviruses described herein can be found, for example, in U.S. Pat. No. 6,716,823, which is incorporated herein by reference.

An effective amount of the pharmaceutical composition is determined based on the intended goal, for example vaccination of a human or non-human subject. The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes nucleic acids or viruses. Generally, the pharmaceutical compositions described herein are administered for the purpose of stimulating and/or enhancing an immune response for example, an immune response against a viral antigen.

When administering an nucleic acid, facilitators of nucleic acid uptake and/or expression can also be included, such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, for example, *Liposomes: A Practical Approach*, RPC New Ed., IRL Press, 1990). Cationic lipid preparations are also well known vehicles for use in delivery of nucleic acid molecules. Suitable lipid preparations include DOTMA (N-[1-(2,3-dioleyloxy)propyl]-N,N,N-trimethylammonium chloride), available under the tradename LIPOFECTIN®, and DOTAP (1,2-bis(oleyloxy)-3-(trimethylammonio)propane). See, for example, Felgner et al., *Proc. Natl. Acad. Sci. U.S.A.* 84:7413-7416, 1987; Malone et al., *Proc. Natl. Acad. Sci. U.S.A.* 86:6077-6081, 1989; U.S. Pat. Nos. 5,283,185 and 5,527,928, and International Publication Nos. WO 90/11092, WO 91/15501 and WO 95/26356. These cationic lipids may preferably be used in association with a neutral lipid, for example DOPE (dioleyl phosphatidylethanolamine). Still further transfection-facilitating compositions that can be added to the above lipid or liposome preparations include spermine derivatives (see, for example, International Publication No. WO 93/18759) and membrane-permeabilizing compounds such as GALA, Gramicidine S and cationic bile salts (see, for example, International Publication No. WO 93/19768).

Alternatively, nucleic acids (such as adenovirus vectors) can be encapsulated, adsorbed to, or associated with, particulate carriers. Suitable particulate carriers include those derived from polymethyl methacrylate polymers, as well as PLG microparticles derived from poly(lactides) and poly (lactide-co-glycolides). See, for example, Jeffery et al., *Pharm. Res.* 10:362-368, 1993. Other particulate systems and polymers can also be used, for example, polymers such as polylysine, polyarginine, polyornithine, spermine, spermidine, as well as conjugates of these molecules.

An appropriate effective amount can be readily determined by one of skill in the art. Such an amount will fall in a relatively broad range that can be determined through routine trials, for example within a range of about 10 μg to about 1 mg. However, doses above and below this range may also be found effective.

Nucleic acids can be coated onto carrier particles (for example, core carriers) using a variety of techniques known in the art. Carrier particles are selected from materials which have a suitable density in the range of particle sizes typically used for intracellular delivery from an appropriate particle-mediated delivery device. The optimum carrier particle size will, of course, depend on the diameter of the target cells. Alternatively, colloidal gold particles can be used wherein the coated colloidal gold is administered (for example, injected) into tissue (for example, skin or muscle) and subsequently taken-up by immune-competent cells.

Tungsten, gold, platinum and iridium carrier particles can be used. Tungsten and gold particles are preferred. Tungsten particles are readily available in average sizes of 0.5 to 2.0 μm in diameter. Although such particles have optimal density for use in particle acceleration delivery methods, and allow highly efficient coating with DNA, tungsten may potentially be toxic to certain cell types. Gold particles or microcrystalline gold (for example, gold powder A1570, available from Engelhard Corp., East Newark, N.J.) will also find use with the present methods. Gold particles provide uniformity in size (available from Alpha Chemicals in particle sizes of 1-3 μm, or available from Degussa, South Plainfield, N.J. in a range of particle sizes including 0.95 μm) and reduced toxicity.

A number of methods are known and have been described for coating or precipitating DNA or RNA onto gold or tungsten particles. Most such methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module or cassette, or loaded into a delivery cassette for use in a suitable particle delivery instrument, such as a gene gun. Alternatively, nucleic acid vaccines can be administered via a mucosal membrane or through the skin, for example, using a transdermal patch. Such patches can include wetting agents, chemical agents and other components that breach the integrity of the skin allowing passage of the nucleic acid into cells of the subject.

Therapeutic compositions that include a disclosed therapeutic agent can be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions including a disclosed therapeutic agent are administered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracistemally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In a supplemental method, any of these immunotherapies is augmented by administering a cytokine, such as interleukin (IL)-2, IL-3, IL-6, IL-10, IL-12, IL-15, GM-CSF, or interferons. In a further method, any of these immunotherapies is augmented by administering an additional chemotherapeutic agent. In one example, this administration is sequential. Examples of such agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), anti-estrogens (such as tamoxifen), and androgens (such as testosterone proprionate and fluoxymesterone). Examples of the most commonly used chemotherapy drugs that can be concurrently administered with the disclosed immunotherapy include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

DNA sequences encoding a sCD27 polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding a sCD27 polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Host cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a sCD27 polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

III. Examples

The interaction between CD27 and its ligand CD70 has been implicated in regulating cellular immune responses to cancer. The role of soluble CD27 (sCD27) in T-cell activation and its elevation in the serum of cancer patients after immunotherapy was investigated. In vitro, sCD27 is preferentially derived from activated CD4+ T cells. Adding sCD27 to stimulated peripheral blood mononuclear cells increases T-cell activation and proliferation, and is associated with the immunological synapse-related proteins myosin IIA, HMGB1, and the TCR V chain. The pool of serum sCD27 was shown to be greater in healthy donors than in cancer patients. However, metastatic cancer patients treated with immunotherapy showed a significant increase in the serum sCD27-pool post-therapy ($p<0.0005$); there was also an increased trend towards an association between enhanced sCD27-pool post-therapy and overall survival ($p=0.022$).

Example 1

Materials and Methods

This Example describes the materials and methods used in Examples 2-5.

Subjects: Serum samples from healthy donors were purchased from Innovative Research (Novi, Mich.) and Valley Biomedical (Winchester, Va.). Cancer patients' sera were obtained from clinical trials conducted at the National Cancer Institute (http://clinicaltrials.gov). Pretreatment serum samples were obtained from the following trials: (1) Vaccine therapy in treating patients with stage D0 prostate cancer (NCT00514072), (2) prostate cancer patients with nonmetastatic castration resistant prostate cancer (CRPC) (D0.5) (NCT00020254) (Mandan et al., Clin. Cancer Res. 14: 4526-4531, 2008.), and (3) a second-generation poxviral vaccine (PSA-TRICOM§®) targeting prostate-specific antigen (PSA) in metastatic CRPC (NCT00060528) (Mandan et al., 2008, supra). Pre- and post-treatment serum samples were obtained from prostate cancer patients treated with ipilimumab (anti-cytotoxic T-lymphocyte antigen 4 (anti-CTLA4)) in combination with PROSTVAC® (NCT00113984). This study enrolled 30 patients to four sequential treatment cohorts. Patients in each cohort received a fixed dose of PROSTVAC® vaccine plus 1, 3, 5, or 10 mg/kg of ipilimumab (Mandan et al., Lancet Oncol. 13: 501-508, 2012). Vaccine was given on days 1, 15, 43 and 71, with ipilimumab given concurrently starting with the second dose of vaccine. For patients who were still alive, the date of the last follow-up was used in the data analysis. Healthy donors' PBMC samples were isolated from the Buffy coat by density gradient centrifugation (MP Biomedicals, Solon, Ohio).

Measurement of sCD27: Serum levels of sCD27 were determined by ELISA using kits from eBioscience (San Diego, Calif.) and Sanquin (Amsterdam, Netherlands).

Human T cell Activation: PBMCs (1×106/ml) from healthy donors were stimulated with anti-CD3/CD28 T-cell activation beads (Invitrogen, Carlsbad, Calif.) at a bead:cell ratio of 1:1, or 1:5 in some experiments, along with 10 U/ml of IL-2 for 15 days. The supernatant was collected on days 3, 7, and 15. PBMCs were also treated with 20 ng/ml PMA (Sigma-Aldrich, St. Louis, Mo.) and 1 µM ionomycin (Sigma) in the presence of 2 µM of the intracellular transport inhibitor monensin (Sigma) for 6 h. The supernatant was tested for sCD27 and cells were analyzed for surface markers and intracellular IFN-γ.

Antibodies and flow cytometry analysis: Percentages of CD8, CD3, CD25, CD27, and CD70 expression on the surface of PBMCs were determined by flow cytometry. Direct-staining mAbs were used to detect each of the cell-surface antigens. PerCP-Cy5.5 antihuman CD4 and CD8 (eBioscience) were used to detect the presence of cell-surface CD4 and CD8. PE mouse antihuman CD3 (BD Biosciences, San Jose, Calif.) and PE mouse antihuman CD70 (BD Biosciences) were used to detect CD3 and CD70, respectively. APC mouse antihuman CD25 (BD Biosciences) and APC-conjugated antihuman CD27 (eBioscience) were used to detect CD25 and CD27, respectively. Cell-surface expression was measured by flow cytometry (FACSCALIBUR™, BD Biosciences) and the resulting data were analyzed using FLOWJO® software (Tree Star Inc., Ashland, Oreg.).

T-Cell subsets isolation: Four T-cell subsets (CD4$^+$ naïve, CD4$^+$ memory, CD8+ naïve and CD8+ memory) were isolated from PBMCs of healthy donors using Miltenyi separation beads (Miltenyi Biotec, Auburn, Calif.). The purified cell subsets were tested by FACS analysis for surface markers: CD4+ naïve cells were CD4$^+$CD45RA$^+$, CD4$^+$ memory cells were CD4$^+$CD45RO$^+$, CD8 naïve cell were CD8$^+$CD56$^-$CD57$^-$CD45RO$^-$, and CD8 memory cells were CD8$^+$CD45RO$^+$CD45RA$^-$CD56$^-$CD57$^-$.

Fluorescence immnuohistochemistry staining: T cells were prepared on slides using cytospin, and fixed with acetone for 30 min, followed by a two-step staining method. The primary antibodies were mouse anti-human Myosin IIA (1:25 dilution) (BD Bioscience) and mouse anti-human 6× His-Tag biotin labeled antibody (1:50 dilution) (AnaSpec, Inc., Fremont, Calif.). The secondary antibodies were FITC Streptavidin (BD Bioscience) and goat anti-mouse Rhodamine (Invitrogen).

Cell proliferation assay: PBMCs (1×107/ml) were labeled with 5 µM CFSE (Invitrogen) according to the manufacturer's instructions. The cells were then stimulated with anti-CD3/CD28 beads in the presence or absence of different amounts of sCD27. Four days after stimulation, FACS analysis was performed.

sCD27 depletion: To deplete sCD27, plates were coated with antihuman CD27 antibody or IgG control (20 µg/ml) (R&D Systems Inc., Minneapolis, Minn.) for 3 h at room temperature or overnight at 4° C. Plates were then washed three times with PBS. Serum derived from a healthy donor or purified recombinant sCD27 was added to the culture and incubated for 2 h. Following incubation, the serum or recombinant sCD27 was tested by ELISA to confirm depletion, and the supernatant of sCD27-depleted serum or recombinant human sCD27 was used for the coculture experiments.

Human sCD27 synthesis and purification: Recombinant human sCD27 protein was purified from the supernatant of HEK 293 cells that were transduced with a construct encoding the extracellular domain (aa 1 to 189) of CD27 protein (GENEART, Regensburg, Germany).

Immunoprecipitation and protein identification: Proteins associated with sCD27 were isolated using sCD27-his (6×) incubated with lysate of anti-CD3/CD28 bead-stimulated PBMCs derived from four healthy donors. ProFound™ Pulldown PolyHis Protein:Protein Interaction Kit was used for immunoprecipitation (Thermo Scientific, Rockford, Ill.). Purified proteins were separated by SDS-PAGE and stained using SimpleBlue (Invitrogen). Protein identification was performed using mass spectrometry as previously described (Zofall et al., Nature 461: 419-422, 2009).

Example 2

In Vitro Production of sCD27 from Activated Human pBMCs

Figure 1B:
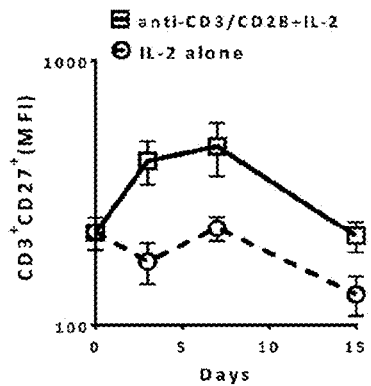
Figure 1C:
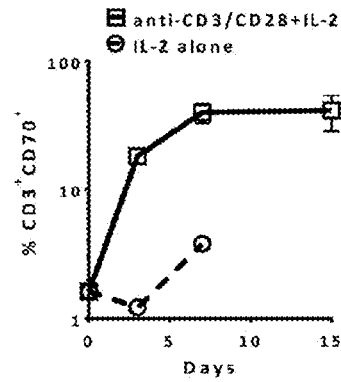
Figure 1D:
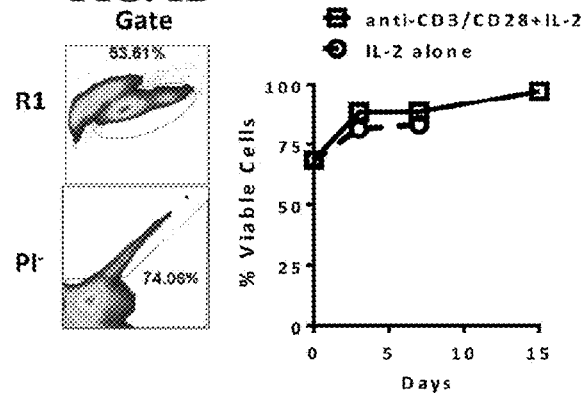

The effect of sCD27 production upon T-cell stimulation and its association with surface expression of CD27 on T cells was investigated. Stimulating PBMCs derived from healthy donors with anti-CD3/CD28 beads plus IL-2 (20 U/ml) or IL-2 alone resulted in a linear increase in sCD27 production, and the highest level of sCD27 was seen in the supernatant on day 15. This could be the result of more T cells accumulated in the wells, and/or more sCD27 shed from each T cell (FIG. 1A). CD27 expression was analyzed on CD3+ T cells to determine the change in expression of membrane-bound CD27 during stimulation. Results suggested a transient increase followed by a decline in surface expression after anti-CD3/CD28 plus IL-2 stimulation (FIG. 1B). In addition, CD70-expressing T cells were enriched upon activation (FIG. 1C), and the production of sCD27 correlated linearly with the amount of CD70-expressing CD8+ T cells in the culture (FIG. 7). Moreover, results suggest that CD70-transduced T cells show enhanced anti-tumor activity and IL-2 production. The status of cell death after the T-cell specific stimulation was evaluated. The results suggested that there was minimal cell death during the course of in vitro activation (FIG. 1D). These data demonstrated that T-cell activation increased sCD27 production, which more likely was the result of shedding from the T cells' surface, rather than activation-induced cell death of T cells, because >90% of the PBMCs were viable 15 days after the stimulation.

Example 3

Factors that Influence sCD27 Production

Figure 2A:
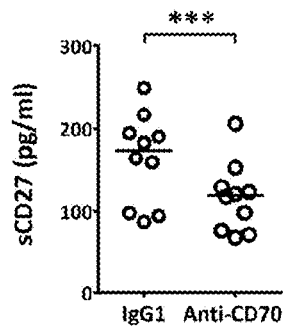
Figure 2B:
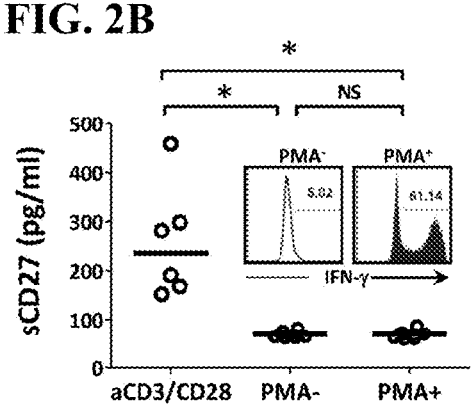

The factors that can alter sCD27 production and which T-cell subsets are the major source for its production were determined. In an experiment using an antibody that blocked CD70, there was a significant inhibition of sCD27 production (FIG. 2A), demonstrating that the shedding of CD27 from T cells is enhanced by ligation of CD27 with its ligand CD70, which has been shown to be expressed on activated T cells (Huang et al., J. Immunother. 28: 258-2672005; Huang et al., J. Immunol. 176: 7726-7735, 2006). Next, the production of sCD27 triggered by either T-cell receptor/CD3 plus CD28 or by PMA-ionomycin, which bypasses the TCR/CD3 signal, were compared. It has previously been reported that PMA-ionomycin stimulation suppresses CD27 surface expression on T cells (de Jong et al., J. Immunol. 146: 2488-2494, 1991). After stimulation with PMA-ionomycin, T cells produced increased amounts of IFN-γ, a sign of activation, but a minimal production of sCD27 was seen compared to that obtained by TCR/CD3/CD28 stimulation (FIG. 2B). These data suggest that TCR/CD3 engagement is necessary for the efficient production of sCD27.

Figure 2C:
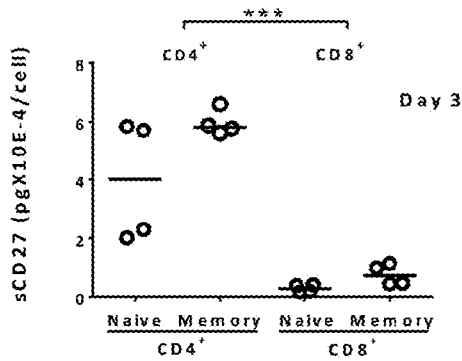
Figure 2D:
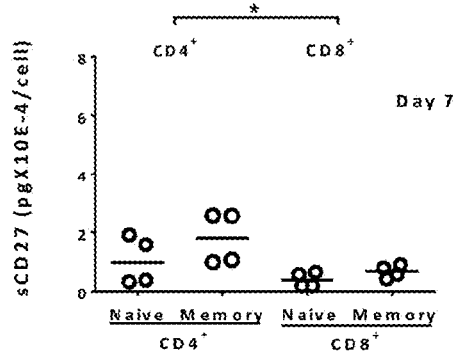
Figure 2E:
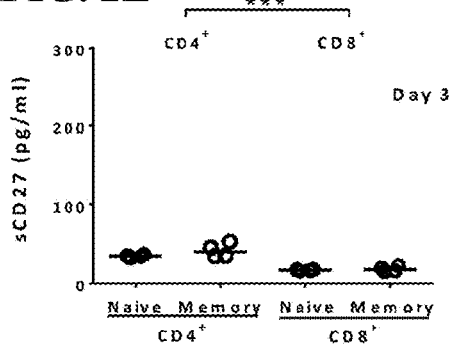
Figure 2F:
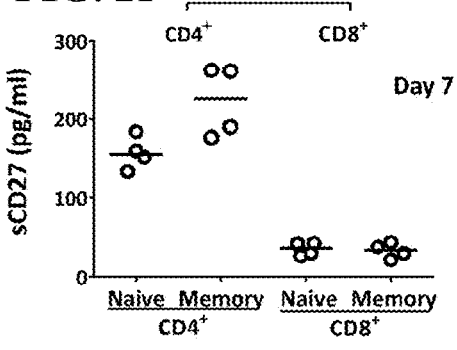

Finally, the difference in sCD27 production was tested among four T-cell subsets: naïve $CD4^+$ and $CD8^+$ and memory $CD4^+$ and $CD8^+$ T cells in sCD27 production 3 and 7 days after activation. The results illustrated that relatively more sCD27 was produced per $CD4^+$ T cell (in particular, CD4+ memory T cell) on day 3 compared with $CD8^+$ T cells, and this was also true for day 7, but with less significance between $CD4^+$ and $CD8^+$ T cells (FIGS. 2C, 2D). Next, the total sCD27 production was evaluated in the supernatant during the T-cell stimulation. Relatively more sCD27 was accumulated in the culture supernatant on day 7 for the $CD4^+$ T cells than the $CD8^+$ T cells (FIGS. 2E, 2F). Taken together, the data suggest that T-cell activation results in the production of sCD27, and that TCR/CD3 signaling and CD70 engagement are necessary for the optimal production of this soluble molecule. CD4+ T cells may be the predominant source for the sCD27 production upon T-cell activation.

Example 4

In Vitro T-Cell Activation by Recombinant sCD27

Figure 3A:
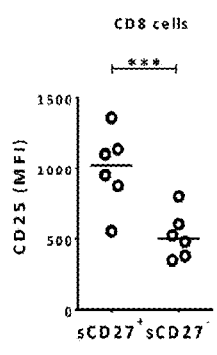
Figure 3B:
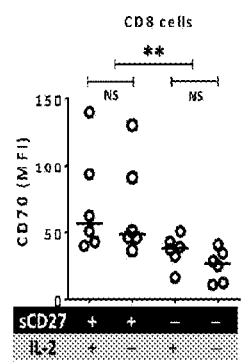
Figure 3C:
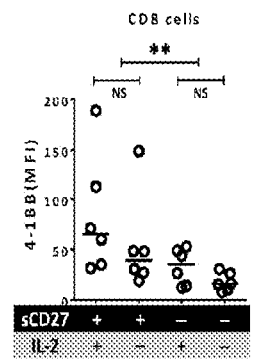
Figure 3D:
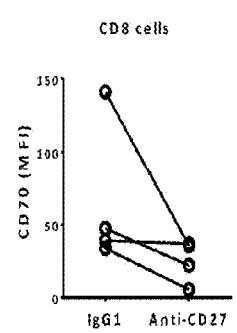
Figure 3E:
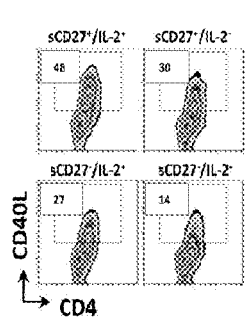
Figure 3F:
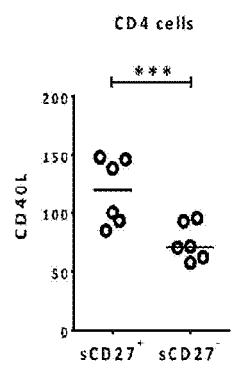
Figure 3G:
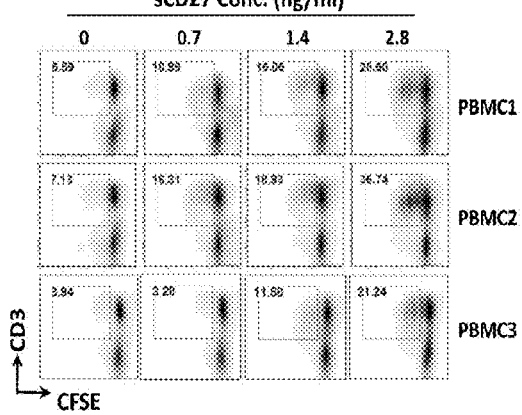

To further test the hypothesis that sCD27 is not only a by-product of T-cell activation but also a functional molecule, recombinant human sCD27 was used to evaluate its functionality. Analysis of T-cell activation markers by FACS analysis showed significant up-regulation of CD25, CD70, and 4-1BB (CD137) expression on $CD8^+$ T cells 3 days after the addition of sCD27. These markers are important for CD8 cytotoxic function, and were only minimally expressed on CD8+ T cells before stimulation (FIGS. 3A, 3B, 3C), suggesting that sCD27's capability for T-cell activation is similar to that of IL-2. Based on this analysis, the effect of sCD27 alone on upregulation of these markers was highly significant ($p<0.0001$ for CD70 and $p <0.005$ for 4-1BB) (FIGS. 3B, 3C). In order to ensure that this effect was specifically due to the presence of sCD27, a procedure using CD27-specific antibody to remove sCD27 was performed. The results showed that CD70 on T cells was decreased in three out of four samples, and CD25 expression on the T cells was also attenuated when sCD27 was depleted, suggesting potential involvement of sCD27 in T-cell activation (FIG. 3D and FIG. 7A). In addition, there was a significant difference in CD25 expression on CD8+ T cells after culture in medium supplemented with serum that contained high (>1000 pg/ml) or low (<10 pg/ml) levels of sCD27 (FIG. 7B). CD4+ T-cell activation was analyzed by testing CD40L expression on CD4+ T cells, a crucial surface marker for the CD4+ T-cell function. The data illustrated enhanced CD40L expression on CD4+ T cells with the addition of sCD27 (FIGS. 3E, 3F). Finally, T-cell proliferation was enhanced in a dose-dependent manner with increasing amounts of recombinant sCD27 and stimulation with a low (1:5) CD3/CD28 bead to cell ratio. The rationale for using a minimum stimulus to the T cells is to mimic the insufficient antigenic stimulation of 13 tumor cells (FIG. 3G). These results provide evidence that sCD27 is a functional molecule involved in T-cell activation.

Example 5

Proteins Potentially Associated with sCD27

It is disclosed above that sCD27 is a potential functional protein. In addition, soluble receptors shed from the cell surface may have different binding patterns or function (due to refolding) than their membrane-bound counterparts. To find molecules that could interact with sCD27, recombinant sCD27 his-tag was used as a bait protein to identify binding partners in a lysate of activated PBMCs. Three immunological synapse-related proteins, myosin IIA, high-mobility group box 1 (HMGB1), and TCR V chain, were identified as potential binding partners for sCD27. No peptide sequence of CD70 was identified in the assay, since there was no CD70 expression on any cell type in the PBMCs (Huang et al., J. Immunother. 28: 258-267, 2005; Huang et al., J. Immunol. 176: 7726-7735, 2006), and the bait protein sCD27 was seen only in the positive lane. Among these three proteins, myosin IIA and HMGB1 showed some background in the control lane, but none was seen for the TCR V chain (Table I).

TABLE I

Proteins with potential to interact with sCD27 after T-cell activation

| Protein¶ | TPC* in Lane 2 (positive) | TPC in Lane 4 (background) | Gene | Accession No. |
| --- | --- | --- | --- | --- |
| Myosin IIA | 79 | 14 | MYH9 | P35579 |
| High mobility group protein B1 | 44 | 5 | HMGB1 | P09429 |
| TCR-Vβ chain | 25 | 0 | TCRBV | N/A |
| CD27§ | 13 | 0 | TNFRSF7 | P26842 |

Proteins associated with sCD27 were isolated using sCD27-his incubated with a lysate of anti-CD3/CD28 bead-stimulated PBMCs derived from four healthy donors. The PROFOUND ™ Pull-down PolyHis Protein: Protein Interaction Kit was used for immunoprecipitation. Purified proteins were separated by SDSPAGE and stained using Simple Blue. Protein identification was performed using mass spectrometry. Each protein was identified based on the sequence and amount of peptides that eluted from the positive and control lanes. The total peptide count in the positive lane had to be 5-fold higher than the control. In descending order, these proteins showed the most potential for interaction with sCD27, based on total peptides eluted from the positive lane.
§Peptides derived from bait protein CD27 were detected only in the positive lane.
*TPC, total peptide count.

In addition, an experiment was performed using immunohistochemistry to confirm these observations. Confocal microscopy showed that sCD27 and myosin IIA were co-localized in activated T cells (FIG. 8), which confirms the previous findings. These data further showed that sCD27 may be associated with the T-cell synapse during the process of T-cell activation.

Example 6

Figure 4A:
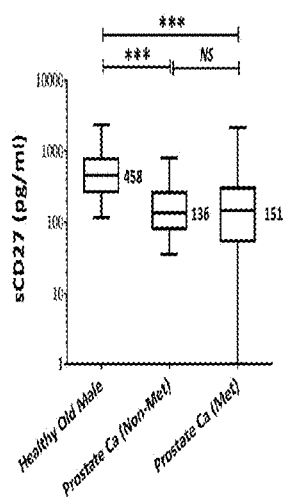
Figure 4B:
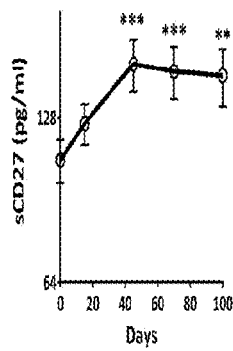

Healthy Donors have a Relatively Larger Serum Pool of sCD27 than Patients with Cancer, and Immunotherapy with pROSTVAC® Plus Ipilimumab Elevated the Pool in these Patients Serum samples from age and gender matched healthy donors and patients with prostate cancer were evaluated for sCD27. Here, "sCD27-pool" is used, which refers to the varying levels of sCD27 in serum, and it was found that this pool was significantly larger in healthy donors than in prostate cancer patients with either metastatic or nonmetastatic disease (p<0.0001; FIG. 4A). This observed difference was not due to the quality of the serum samples, since the samples were also tested for another soluble protein, sCD40L, which appeared in reverse proportions to sCD27 in healthy donors and cancer patients (Huang et al., Blood 120: 3030-3038, 2012). In addition, PBMCs derived from healthy donors and cancer patients were compared for the production of sCD27 upon in vitro stimulation (FIG. 9). There were no differences in the frequency of CD3+CD27+ T cells between healthy donors and cancer patients, and no differences in the amounts of sCD27 in supernatants after 3-15 days of in vitro culture.

Figure 4C:
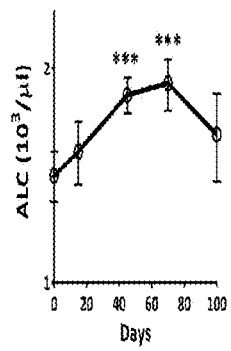
Figure 4D:
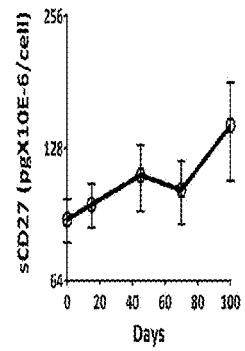

Results of a recently completed clinical trial of PROSTVAC® vaccine in combination with ipilimumab (anti-CTLA4) in patients with metastatic CRPC offer insights into an association between increased serum sCD27 and clinical outcomes (Madan et al., Lancet Oncol. 13: 501-508, 2012). PROSTVAC® is a poxviral-based vaccine targeting prostate-specific antigen (PSA) and containing transgenes for three costimulatory molecules (B7.1, ICAM-1 and LFA-3, designated TRICOM). A randomized, placebo-controlled, multi-center trial with this vaccine demonstrated improved patient survival (Kantoff et al., J. Clin. Oncol. 28: 1099-1105, 2010). Ipilimumab, a fully human mAb against a negative immune modulator, CTLA-4, has been used as monotherapy or in combination therapy and has been demonstrated to induce durable objective responses in patients with advanced melanoma (Hodi et al., Proc. Natl. Acad. Sci. USA 100: 4712-4717, 2003; Downey et al., 2007, Clin. Cancer Res. 13: 6681-6688). This study enrolled 30 patients to four sequential treatment cohorts. Patients in each cohort received PROSTVAC® plus 1, 3, 5, or 10 mg/kg of ipilimumab. Overall, there was no clear trend observed between distributions of serum sCD27 and the dose of ipilimumab. It should be noted, however, that 3/3 patients in the 1 mg/kg cohort and 3/6 patients in the 3 mg/kg cohort had received prior chemotherapy. A comparison of pre- and post-treatment levels of sCD27 in these patients found a significant increase in serum sCD27-pool as early as 45 days, which was 4 weeks after the first dose of ipilimumab (p<0.001, FIG. 4B). These increases in sCD27 levels were in accordance with the slight increases in absolute lymphocyte count (FIG. 4C). In addition, there was a discrete (but statistically non-significant, p>0.40) increase in sCD27 production per lymphocyte after treatment (FIG. 4D).

Figure 5A:
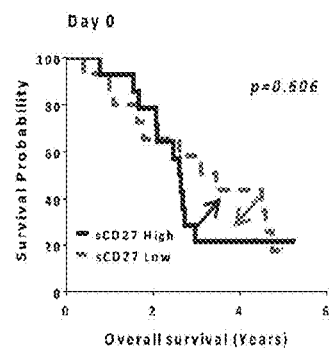
Figure 5B:
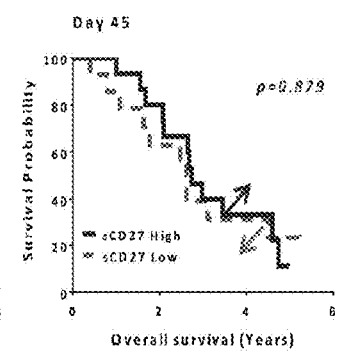
Figure 5C:
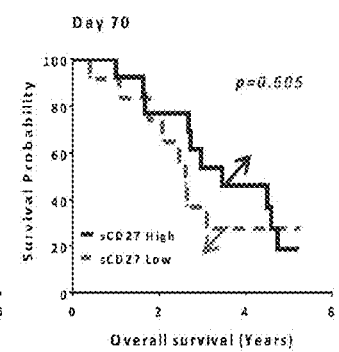
Figure 5D:
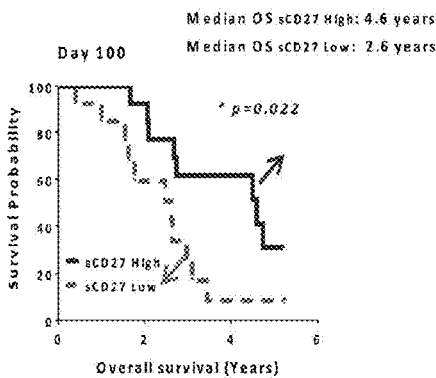
Figure 5E:
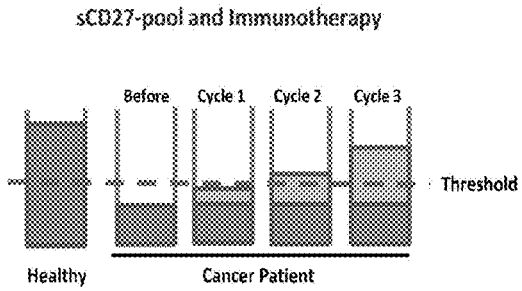

Example 7 sCD27-Pool Level Elevation Associated with Clinical Outcomes for Patients Treated with PROSTVAC® Plus Ipilimumab The sCD27-pool in cancer patients can be significantly enlarged by immunotherapy. Next it was determined whether this sCD27 increase can bring a positive effect on clinical outcome for these patients. First patients were separated into two groups using median values of sCD27 on day 0, and increased sCD27 (differences from day 0) for the post-treatment days and then the association between sCD27 and overall survival was evaluated. No differences were seen between the two groups on day 0 (FIG. 5A, p=0.606) and day 45 (FIG. 5B, p=0.879). However, a gap emerged (as indicated in blue and red arrows) between groups on day 70, which was 4 weeks after the second dose of ipilimumab (FIG. 5C, p=0.605), and a strong trend was observed at 100 days (FIG. 5D, p=0.022, a trend). The median overall survival was 4.6 years in the sCD27 high group, which was 2 years longer than for patients in the sCD27 low group, suggesting that patients who had a gain of sCD27-pool after the treatment may have a better chance of surviving longer. In order to clearly describe our interpretation and hypothesis, a schema is shown in FIG. 5E. It was assumed that there is a putative threshold (red dashed line) for the pool of sCD27, which is a minimum level that is required for proper anti-tumor immunity in humans. The data shown above indicated that immunotherapy can help some patients to raise their sCD27-pool levels, which could bring a positive clinical outcome for these patients. The data illustrate that sCD27 can contribute to tumor immunity.

These results document that production of sCD27 requires ligation of CD27 with CD70. T-cell activation that bypassed the TCR produced minimal sCD27, indicating that TCR engagement is an important factor in the shedding of sCD27. IL-2 alone can also induce a similar amount of sCD27 without significant CD70 expression on T cells, compared with anti-CD3/CD28 plus IL-2, suggesting a distinct mechanism may be involved in its induction of sCD27. This finding is consistent with a previous study illustrating that IL-2 can dramatically decrease CD27 expression on the T-cell surface (Huang et al., J. Immunol. 176: 7726-7735, 2006). The examination of four T-cell subsets for sCD27 production upon in vitro stimulation showed that all subsets produced sCD27, and CD4$^+$ memory T cells produced relatively more sCD27 per cell. The in vitro results suggest another potential role of memory CD4+ T cells in immune regulation.

To test the functionality of sCD27, PBMCs were stimulated in vitro with varying combinations of purified recombinant sCD27 protein and IL-2. Stimulation with sCD27 provided a strong proliferative signal and induced increased lymphocyte proliferation compared with IL-2. A previous study showed that IL-2 modulates CD27 and CD70 expression on T cells, indicating that the immunological action of IL-2 may be through the CD27-CD70 signaling pathway (Huang et al., supra, 2006). More importantly, markers of T-cell activation were significantly up-regulated after the addition of sCD27. These activation markers have been shown to be critical to the cytotoxic activity of CD8+ T cells (Huang et al., supra, 2006; Gluchkova et al., J. Immunol. 182: 718-725, 2009; Halstead et al., Nat. Immunol. 3: 536-541; Wilcox et al., J. Clin. Invest. 109: 651-659.), and were expressed minimally or not at all on CD8+ T cells prior to stimulation. Furthermore, CD4+ T cells in PBMCs showed enhanced CD40L surface expression after stimulation, an effect that may facilitate B-cell function as well as dendritic-cell maturation and CD8+ T-cell priming (Nolte et al., Immunol. Rev. 229: 216-231, 2009).

The in vitro data indicating that sCD27 can help to up-regulate CD70 expression on T cells, in addition to the fact that sCD27 pre-exists at a high level in healthy individuals, suggest that sCD27 may be involved in the induction of CD70 expression on T cells upon activation, a signal that is crucial for potent T-cell activation (Huang et al., op. cit., 2009). Finally, the search for proteins that could potentially be associated with sCD27 revealed a protein complex composed of three protein sequences: myosin-IIA, HMGB1, and the TCR Vβ chain. Myosin IIA, the most abundant protein in cells, has been shown to play a central role in the formation and persistence of the immunological synapse and T-cell signaling (Ilani et al., Nat. Immunol. 10: 531-539, 2009). Inhibition of myosin IIA decreases the association of active ZAP-70 with TCR (Yu et al., PLoS ONE 7: e30704, 2012). The above data showed that sCD27 is co-localized with myosin IIA in activated T cells (FIG. 8), implying that sCD27 may be associated with myosin IIA directly or via other proteins in the complex. In addition, a previous study illustrated a direct association between myosin IIA and TCR (Ilani et al., op. cit., 2009), and the finding of the TCR Vβ chain in the complex of sCD27 pulling down further indicates that sCD27 is closely related to the T-cell synapse. To date, CD70 is the only ligand found to bind to the extracellular domain of membrane-bound CD27. The intracellular domain of CD27 was found to bind to SIVA, a proapoptotic protein (Prasad et al., Proc. Natl. Acad. Sci. USA 94: 6346-6351, 1997). In the experiments disclosed above, CD70 was not pulled down by sCD27. Two possible explanations may be proposed: First, when receptors are shed from the cell surface, their structure and functionality may alter from the membrane-bound version, which means they may lose the binding site to their ligand. Second, there was minimal or no expression of CD70 on the cell subsets within the PBMCs after overnight stimulation with anti-CD3/CD28.

The finding that levels of serum sCD27 are significantly higher in healthy donors than in cancer patients suggests that cancer patients may produce less sCD27, potentially due to (a) a lack of stimulation due to immunosuppression, which attenuates the shedding of this molecule; (b) immune senescence and exhaustion, which results in the accumulation of more CD27 negative, late stage effector cells; (c) intrinsic defects in sCD27 production. However, no difference was found in sCD27 production during in vitro stimulation, when we compared PBMCs derived from healthy donors and cancer patients (FIG. 9), which ruled out the possibility of an intrinsic defect in the shedding of CD27 in cancer patients.

The findings demonstrated that there was no difference in overall survival between patients who had higher levels of sCD27-pool than another group of patients that had lower levels of sCD27-pool before the therapy. The enlargement of the sCD27-pool in serum after each treatment cycle and its association with overall survival was evaluated. Interestingly, as more treatment cycles were given, a greater association was seen. After three treatment cycles, a statistical significance was revealed for the correlation between the sCD27-pool level elevation and overall survival. Although there was an elevation in absolute lymphocyte count (ALC) after treatment, no correlation between ALC and overall survival was found. Based on the result that healthy donors have a larger sCD27-pool, it was speculated that patients who possessed a relatively larger pool before the treatment should have a better clinical outcome. However, the results were surprising; the pre-value was not associated with clinical outcome, but the increased value after three cycles of treatment showed a trend of correlation with overall survival. It was found that with increased treatment cycles, there was a clear separation in overall survival between patients who had an enlargement of the sCD27-pool vs. patients who had a minimum change of this pool. In order to clearly illustrate this data interpretation, a hypothetical schema was drawn (FIG. 5E). In general, the levels of sCD27-pool in cancer patients are very low; even for patients who have relatively higher levels of sCD27, the average level may still be below the threshold that is necessary for proper immune function. However, after multiple treatments of immunotherapy, the pool can be cumulatively refilled for some patients, and when the elevation has reached or crossed the threshold, the benefit of sCD27 may begin to show. In the clinical trial, 34 immune-related adverse events (irAEs) grades 2-4 occurred during 40% of the cycles (Madan et al., Lancet Oncol. 13: 501-508, 2012). Of the 21 patients who experienced an irAE, 13 had elevated sCD27 following treatment. However, no clear trend was observed between values of serum sCD27 and the dose of ipilimumab, or in the correlation between irAE occurrence/grade and elevation of sCD27 in serum.

The studies reported here suggest that sCD27 is a functional protein rather than a mere by-product of T-cell activation, and that it acts as an agonist rather than an antagonist in the process of T-cell activation. sCD27's potential associations with proteins closely related to T-cell activation, effector activity, TCR rearrangement, and synapse formation suggest that sCD27 may be critical to facilitating T-cell activation. In addition, soluble receptors, like cytokines, can function as systemic immune mediators. Assessing the size of sCD27-pool that was elevated by immunotherapy at early time points can provide insightful information for planning therapeutic strategies for cancer patients.

Example 8

Expression of sCD27 in Subjects with Breast Cancer

Serum levels of sCD27 were compared in healthy donors (male and female, n=24) vs. pre samples from patients with breast cancer in the PANVAC-Docetaxel trial (n=33). sCD27 is decreased in the subjects with breast cancer (see FIG. 10).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a subject diagnosed as having a solid tumor or a predisposition to developing a solid tumor, wherein the solid tumor is not a lymphoma, the method comprising:
   diagnosing the subject as having the solid tumor or the predisposition to developing the solid tumor by detecting an amount of soluble CD27 (sCD27) polypeptide present in a serum sample obtained from the subject; and
   comparing the amount of sCD27 polypeptide in the serum sample with a control value indicative of the basal level of sCD27 polypeptide present in the serum of a subject that does not have a solid tumor or a predisposition to developing a solid tumor, wherein a reduction of the amount of sCD27 polypeptide relative to the control value indicates that the subject has the solid tumor or the predisposition to developing the solid tumor; and
   administering to the subject an effective amount of a therapeutic agent to treat the tumor.

2. The method of claim 1, wherein detecting comprises contacting the serum sample with a monoclonal antibody that specifically binds soluble sCD27 or CD70, mass spectrometric analysis or measuring the activity of sCD27.

3. The method of claim 1, wherein the solid tumor is a prostate tumor, a colorectal tumor or a breast tumor.

4. The method of claim 1, wherein the therapeutic agent comprises a poxviral vector encoding at least one co-stimulatory molecule and a tumor antigen.

5. The method of claim 4, wherein the subject has prostate cancer, and wherein the therapeutic agent comprise a poxviral vector encoding prostate specific antigen, B7.1, intracellular adhesion molecule (ICAM)-1 and leukocyte function associated antigen (LFA)-3.

6. A method of treating a subject that is benefiting from a treatment for a solid tumor, wherein the solid tumor is a prostate tumor, a breast tumor, a colorectal tumor, a pancreatic tumor, a renal tumor or a mesothelioma tumor, comprising:
   monitoring disease progression in the subject that is undergoing treatment by detecting an amount of sCD27 present in a first serum sample obtained from a subject at a first time point; detecting an amount of sCD27 present in a second serum sample obtained from a subject at a second later time point; comparing the amount of sCD27 detected in the first serum sample with the amount of sCD27 detected in the second serum sample; and
   detecting an increase in the amount of sCD27 in the second sample relative to the first sample, which indicates that the subject was benefiting from the treatment; and
   administering to the subject a dose of a therapeutic agent.

7. The method of claim 6, wherein detecting comprises contacting the sample with a monoclonal antibody that specifically binds soluble sCD27 or CD70, the mass spectrometric analysis or measuring the activity of sCD27.

8. The method of claim 6, wherein the therapeutic agent comprises a poxviral vector encoding at least one co-stimulatory molecule and a tumor antigen.

9. The method of claim 8, wherein the subject has prostate cancer, and wherein the therapeutic agent comprise a poxviral vector encoding prostate specific antigen, B7.1, intracellular adhesion molecule (ICAM)-1 and leukocyte function associated antigen (LFA)-3.

10. The method of claim 9, wherein therapeutic agent comprises an anti-CTLA4 antibody.

11. A method for treating a subject with a therapeutic agent, the method comprising:
    determining the effectiveness of the therapeutic agent in the subject by quantitating an amount of sCD27 present in a first serum sample from the subject following treatment with the therapeutic agent; and
    detecting a statistically significant increase in the amount of sCD27 detected compared with a control value, wherein the control value is a level of sCD27 present in a second serum sample from the subject obtained prior to the treatment with the therapeutic agent,
    wherein the detection of the statistically significant increase in the amount of sCD27 in the first serum sample as compared to the amount of sCD27 in the second sample indicates that the therapeutic agent is effective for treating the subject; and
    treating the subject with the therapeutic agent, wherein the subject has a solid tumor and the solid tumor is not a lymphoma.

12. The method of claim 11, wherein the therapeutic agent is administered at least three times.

13. The method of claim 11, wherein the therapeutic agent comprises a cancer vaccine.

14. The method of claim 11, wherein the therapeutic agent comprises a poxviral vector encoding at least one co-stimulatory molecule and a tumor antigen.

15. The method of claim 14, wherein the subject has prostate cancer, and wherein the therapeutic agent comprise a poxviral vector encoding prostate specific antigen, B7.1, intracellular adhesion molecule (ICAM)-1 and leukocyte function associated antigen (LFA)-3.

16. The method of claim 15, wherein the therapeutic agent comprises an anti-cancer antibody.

17. The method of claim 16, wherein the anti-cancer antibody is an anti-CTLA4 antibody.

18. The method of claim 11, wherein the solid tumor is a pancreatic tumor, a renal tumor or a mesothelioma tumor.

* * * * *